United States Patent [19]

Tsujihara et al.

[11] 4,241,052
[45] Dec. 23, 1980

[54] NOVEL NITROSOUREA COMPOUNDS AND PROCESS FOR PREPARING THE SAME

[75] Inventors: Kenji Tsujihara, Urawa; Masakatsu Ozeki, Wako; Yoshihisa Arai, Urawa, all of Japan

[73] Assignee: Tanabe Seiyaku Co., Ltd., Osaka, Japan

[21] Appl. No.: 38,638

[22] Filed: May 14, 1979

[30] Foreign Application Priority Data

Jun. 10, 1978 [GB] United Kingdom ............... 26659/78
Jan. 27, 1979 [GB] United Kingdom ............... 2955/79

[51] Int. Cl.³ .................. A61K 31/70; C07H 13/12; A61K 31/73
[52] U.S. Cl. .................. 424/180; 536/22; 536/53; 536/18
[58] Field of Search .................. 424/180; 536/53, 22

[56] References Cited

U.S. PATENT DOCUMENTS

| | | | |
|---|---|---|---|
| 3,577,406 | 5/1971 | Hessler | 536/53 |
| 4,086,415 | 4/1978 | Suami et al. | 536/53 |
| 4,156,777 | 5/1979 | Kimura | 536/53 |
| 4,157,439 | 6/1979 | Suami | 536/53 |

OTHER PUBLICATIONS

Noller "Chemistry of Organic Compounds," W. B. Saunders Co., Philadelphia, Pa., 1965, p. 598.

*Primary Examiner*—Johnnie R. Brown
*Attorney, Agent, or Firm*—Bierman & Bierman

[57] ABSTRACT

A nitrosourea compound of the formula:

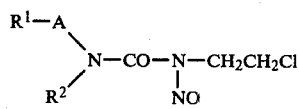

wherein $R^1$ is an alicyclic group having 3 to 6 carbon atoms, phenyl, phenyl substituted with one to substituents selected from halogen, lower alkyl, lower alkoxy, hydroxy and nitro, or a heteromonocyclic group selected from oxiranyl, tetrahydrofuryl, 1,3-dioxolanyl, 1,4-dioxanyl, morpholino, tetrahydro-S,S-dioxo-thienyl, furyl, thienyl and pyridyl; $R^2$ is aldopentofuranosyl, aldo-pentopyranosyl, aldo-hexopyranosyl or O-aldo-hexopyranosyl-(1→4)-aldo-hexopyranosyl; and A is a single bond or straight or branched alkylene having one to 3 carbon atoms, is prepared by nitrosation of a compound of the formula:

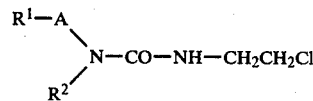

wherein $R^1$, $R^2$ and A are the same as above. Said nitrosourea compound is useful as an anti-tumor or anti-leukemic agent however, effectiveness in human beings has not yet been demonstrated.

48 Claims, No Drawings

NOVEL NITROSOUREA COMPOUNDS AND PROCESS FOR PREPARING THE SAME

This application claims the priority of British Applications 26659/78 and 7902955/79, filed June 10, 1978 and Jan. 27, 1979, respectively.

This invention relates to a novel nitrosourea compound and a process for preparing the same. More particularly, it relates to a compound of the formula:

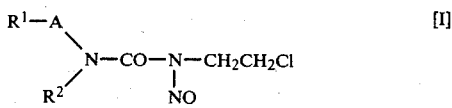

wherein $R^1$ is alicyclic group having 3 to 6 carbon atoms, phenyl, phenyl substituted with one to 3 substituents selected from the class consisting of halogen, lower alkyl, lower alkoxy, hydroxy and nitro, or a heteromonocyclic group selected from the class consisting of oxiranyl, tetrahydrofuryl, 1,3-dioxolanyl, 1,4-dioxanyl, morpholino, tetrahydro-S,S-dioxo-thienyl, furyl, thienyl and pyridyl; $R^2$ is aldopentofuranosyl, aldo-pentopyranosyl, aldo-hexopyranosyl or O-aldo-hexopyranosyl-(1→4)-aldo-hexopyranosyl; and A is single bond or straight or branched alkylene having one to 3 carbon atoms.

It is known that (N′-chloroethyl-N′-nitrosocarbamoyl)-amino derivatives of monosaccharides are prepared by nitrosation of (N′-chloroethylcarbamoyl)amino-monosaccharides with an alkali metal nitrite such as sodium nitrite (U.S. Pat. No. 4086451 and Japanese Patent Publication (unexamined) Nos. 108043/1975 and 52128/1976). These patents also disclose that 1-(2-chloroethyl)-1-nitroso-3-(D-mannopyranosyl)urea and 1-(2-chloroethyl)-1-nitroso-3-(D-glucopyranosyl)urea (the latter compound being hereinafter referred to as "GANU") increase the life span of mice implanted intraperitoneally with the tumor cells of lymphoid leukemia L-1210. Further, it is known that (N′-chloroethyl-N′-nitrosocarbamoyl)amino derivatives of dissacharides such as 1-(2-chloroethyl)-1-nitroso-3-(D-lactosyl)urea and 1-(2-chloroethyl)-1-nitroso-3-(D-maltosyl)urea are prepared from the corresponding (N′-chloroethylcarbamoyl)amino-disaccharides in the same manner as above and show anti-tumor activity against leukemic cells (Japanese Patent Publication (unexamined) No. 141815/1976).

We have now found that the nitrosourea compound [I] of the present invention shows potent anti-tumor or anti-leukemic activity with low toxicity and is useful to inhibit the growth of malignant tumor cells in warm-blooded animals. For example, when the anti-tumor effects upon leukemia is estimated by administering each drugs intraperitoneally to leukemic cell-inoculated mice (i.e., mice implanted with tumor cells of Leukemia L-1210) for five consecutive days, 1-(2-chloroethyl)-1-nitroso-3-(thiophen-2-yl-methyl)-3-(L-arabinopyranosyl)urea at the dose of 0.35 mg/kg, 1-(2-chloroethyl)-1-nitroso-3-cyclopropylmethyl-3-(L-arabinopyranosyl)urea at the dose of 1.1 mg/kg, 1-(2-chloroethyl)-1-nitroso-3-(oxiran-2-yl-methyl)-3-(L-arabinopyranosyl)urea at the dose of 1.05 mg/kg or 1-(2-chloroethyl)-1-nitroso-3-tetrahydrofurfuryl-3-(D-galactopyranosyl)urea at the dose of 1.7 mg/kg shows an increase of about 30% in the average life span of said mice. Moreover, the nitrosourea compound [I] of the invention is low in toxicity and shows great safety for use as an anti-tumor agent. For example, when the therapeutic index is estimated by the ratio of the optimal dose (the daily dose at which the maximum increase in the life span of tumor cell-inoculated mice occurs) to $ILS_{30}$ (the minimum daily dose which shows 30% increase in the life span of said mice) in case of Leukemia L-1210, said therapeutic indexes of 1-(2-chloroethyl)-1-nitroso-3-(thiophen-2-yl-methyl)-3-(L-arabinopyranosyl)urea, 1-(2-chloroethyl)-1-nitroso-3-tetrahydrofurfuryl-3-(D-galactopyranosyl)urea, 1-(2-chloroethyl)-1-nitroso-3-(α-methylbenzyl)-3-[O-α-D-glucopyranosyl-(1→4)-D-glucopyranosyl]urea and 1-(2-chloroethyl)-1-nitroso-3-phenethyl-[O-α-D-glucopyranosyl-(1→4)-D-glucopyranosyl]urea are about 7 to 12 times greater than that of GANU. The compound [I] may also be characterized by a high therapeutic index estimated in terms of ratio of M.T.D. (the maximum tolerated dose which shows 100% inhibition for the growth of Ehrlich ascites tumor in mice without causing the death of said mice) to M.E.D. (the minimum effective dose which shows 100% inhibition for the growth of said ascites tumor). For example, said therapeutic indexes (M.T.D./M.E.D.) of 1-(2-chloroethyl)-1-nitroso-3-(thiophen-2-yl-methyl)-3-[O-α-D-glucopyranosyl-(1→4)-D-glucopyranosyl]urea, 1-(2-chloroethyl)-1-nitroso-3-(p-methoxybenzyl)-3-[O-α-D-glucopyranosyl-(1→4)-D-glucopyranosyl]urea and 1-(2-chloroethyl)-1-nitroso-3-benzyl-3-[O-α-D-glucopyranosyl-(1→4)-D-glucopyranosyl]urea are about 8 times greater than that of GANU. The compound [I] of the invention may further show low bone marrow toxicity.

In the above-mentioned formula [I], representative examples of the group $R^1$ include alicyclic groups such as cyclopropyl, cyclobutyl, cyclopentyl and cyclohexyl; phenyl; substituted phenyl groups such as monochlorophenyl (e.g., p-chlorophenyl), monomethylphenyl (e.g., p-methylphenyl), trimethylphenyl (e.g., 2,4,6-trimethylphenyl), monomethoxyphenyl (e.g., p-methoxyphenyl), dimethoxyphenyl (e.g., 2,3-dimethoxyphenyl), trimethoxyphenyl (e.g., 3,4,5-trimethoxyphenyl), monohydroxyphenyl (e.g., p-hydroxyphenyl) and mononitrophenyl (e.g., p-nitrophenyl); and heteromonocyclic groups such as oxiranyl, tetrahydrofuryl (e.g., tetrahydrofuran-2-yl), 1,3-dioxolanyl (e.g., 1,3-dioxolan-2-yl, 1,3-dioxolan-4-yl), 1,4-dioxanyl (e.g., 1,4-dioxan-2-yl), morphorino, tetrahydro-S,S-dioxo-thienyl (e.g., tetrahydro-S,S-dioxo-thiophen-3-yl), furyl (e.g., furan-2-yl), thienyl (e.g., thiophen-2-yl) and pyridyl (e.g., pyridin-2-yl). On the other hand, representative examples of the group $R^2$ include aldo-pentofuranosyl such as D-ribofuranosyl and D-deoxyribofuranosyl; aldo-pentopyranosyl such as L-arabinopyranosyl, D-arabinopyranosyl and D-xylopyranosyl; aldo-hexopyranosyl such as D-glucopyranosyl, D-galactopyranosyl, D-mannopyranosyl, L-rhamonopyranosyl, D-fucopyranosyl and D-talopyranosyl; and O-aldo-hexopyranosyl-(1→4)-aldohexoyranosyl such as O-α-D-glucopyranosyl-(1→4)-D-glucopyranosyl (=D-maltosyl) and O-β-D-galactopyranosyl-(1→4)-D-glucopyranosyl (=D-lactosyl). Further, representative examples of the group A include single bond; and straight or branched alkylene such as methylene, ethylene, propylene and methylmethylene.

Among those of the invention, a preferred subgenus includes the compound of the formula [I] in which $R^1$ is alicyclic group selected from the class consisting of cyclopropyl, cyclopentyl and cyclohexyl; phenyl; a substituted phenyl group selected from the class consisting of monochlorophenyl, monomethylphenyl, trimethylphenyl and monomethoxyphenyl; or a heteromonocyclic group selected from the class consisting of oxiranyl, tetrahydrofuryl, furyl and thienyl, $R^2$ is D-aldopentofuranosyl, D- or L-aldo-pentopyranosyl, D-aldohexopyranosyl or O-D-aldo-hexopyranosyl-(1→4)-D-aldo-hexopyranosyl, and A is single bond or alkylene having one or two carbon atoms. Another preferred subgenus includes the compound of the formula [I] in which $R^1$ is alicyclic group selected from the class consisting of cyclopropyl, cyclopentyl and cyclohexyl; phenyl; a substituted phenyl group selected from the class consisting of p-chlorophenyl, p-methylphenyl, 2,4,6-trimethylphenyl and p-methoxyphenyl; or a heteromonocyclic group selected from the class consisting of oxiran-2-yl, tetrahydrofuran-2-yl, furan-2-yl and thiophen-2-yl, and $R^2$ is D-ribofuranosyl, L-arabinopyranosyl, D-xylopyranosyl, D-glucopyranosyl, D-galactopyranosyl or O-α-D-glucopyranosyl-(1→4)-D-glucopyranosyl, and A is single bond or alkylene having one or two carbon atoms. A further preferred subgenus includes the compound of the formula [I] in which $R^1$ is cyclopropyl, cyclohexyl, phenyl, p-methylphenyl, 2,4,6-trimethylphenyl, p-methoxyphenyl, oxiran-2-yl, tetrahydrofuran-2-yl, furan-2-yl or thiophen-2-yl, $R^2$ is L-arabinopyranosyl, D-galactopyranosyl or O-α-D-glucopyranosyl-(1→4)-D-glucopyranosyl, and A is single bond, methylene, ethylene or methylmethylene.

According to the present invention, the nitrosourea compound [I] is prepared by nitrosation of a compound of the formula:

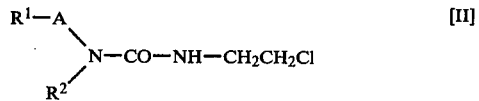

[II]

wherein $R^1$, $R^2$ and A are the same as defined above.

Alternatively, the nitrosourea compound of formula [I] in which $R^1$ is oxiranyl is prepared by nitrosation of a compound of the formula:

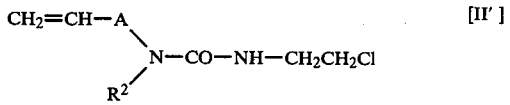

[II']

wherein $R^2$ and A are the same as defined above, followed by epoxidation of the resultant compound of the formula:

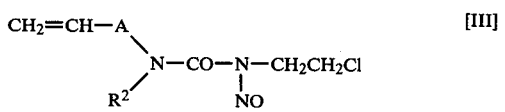

[III]

wherein $R^2$ and A are the same as defined above.

The starting compound [II] or [II'] is readily obtained. For example, it can be prepared by condensing a primary amine of the formula: $R^1$—A—$NH_2$ or $CH_2$=CH—A—$NH_2$ (wherein $R^1$ and A are the same as defined above) with a compound of the formula: $R^2$—OH (wherein $R^2$ is the same as defined above) at about 20° to 80° C. in an inert solvent (e.g., methanol, ethanol) to give a secondary amine of the formula:

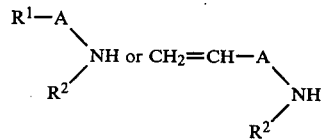

(wherein $R^1$, $R^2$ and A are the same as defined above), and then condensing said secondary amine with 2-chloroethyl isocyanate at 0° to 30° C. in a suitable solvent (e.g., tetrahydrofuran, methanol, ethanol).

The nitrosation of the invention is accomplished by contacting the compound [II] or [II'] with nitrous acid, nitrogen trioxide or nitrogen tetroxide in a suitable solvent. The reaction can be preferably carried out at a temperature of −20° to 20° C., especially at about −10° to about 0° C. Water, lower alkanols (e.g., methanol, ethanol), tetrahydrofuran, methylene chloride, ethyl acetate, acetic acid, formic acid and so forth are used as the solvent. When free nitrous acid is prepared by reacting an alkali metal salt of nitrous acid (e.g., sodium nitrite, potassium nitrite) or a lower alkyl ester thereof (e.g., butyl nitrite, amyl nitrite) with a mineral or organic acid (e.g., hydrochloric acid, sulfuric acid, formic acid, acetic acid and the like), it is preferred that said free nitrous acid is employed for the subsequent nitrosation reaction immediately after preparation thereof. On the other hand, when nitrogen trioxide or nitrogen tetroxide is employed in the invention, it is preferred to carry out the nitrosation reaction by dissolving or suspending the starting compound [II] or [II'] in the suitable inert solvent and then introducing gaseous nitrogen trioxide or tetroxide thereto in the presence or absence of an acid acceptor. Sodium bicarbonate, sodium carbonate, potassium carbonate, sodium acetate, potassium acetate and the like are suitable as the acid acceptor. When the nitrosation reaction is completed, the compound [I] or [III] is readily recovered from the reaction mixture and may be, if required, further purified by silica gel chromatography.

The epoxidation of the invention is accomplished by treating the compound [III] with an oxidizing agent such as meta-chloroperbenzoic acid in a suitable solvent. The reaction can be preferably carried out at a temperature of −10° to 50° C., especially 10° to 30° C. Methylene chloride, chloroform, benzene, acetic acid and so forth are suitable as the solvent. When the epoxidation reaction is completed, the compound [I] ($R^1$=oxiranyl) is readily recovered from the reaction mixture and may be, if required, further purified by silica gel chromatography.

The nitrosourea compound [I] thus obtained shows potent anti-tumor activity against various tumor cells such as Ehrlich's carcinoma, Sarcoma 180, Leukemia L-1210, Lewis lung carcinoma, Yoshida sarcoma, Rat ascites hepatoma and so forth. It may be useful to prolong the survival time of warm-blooded animals afflicted with said tumors and/or minimize the growth of said tumors in said animals. It may also be employed for therapy of malignant lymphoma, leukemia, stomach tumor, hepatoma and other malignant tumors in test animals. However, effectiveness in human beings has not yet been demonstrated. The nitrosourea compound [I] can be used for pharmaceutical use in the form of a pharmaceutical preparation suitable for either oral or parenteral administration. The compound [I] may also be used in conjunction or admixture with a pharmaceutical excipient. The excipient selected should be the one which does not react with the compound [I]. Suitable excipients include, for example, gelatin, lactose, glucose, sodium chloride, starch, magnesium stearate, talcum, vegetable oil and so forth. Other known medicinal excipients may be employed. The pharmaceutical preparation may be a solid dosage form such as a tablet, a coated tablet, a pill or a capsule; or a liquid dosage form such as a solution, a suspension or an emulsion. Further, the compound [I] may be employed in the form of an injection or suppository when administered parenterally. The pharmaceutical preparation may be sterilized and/or may contain auxiliaries such as preserving and stabilizing agents. The dose of the compound [I] for pharmaceutical use depends on route of administration; the age, weight and condition; and the particular disease to be treated. In general, it may be used for pharmaceutical use at a dose of 0.1 to 30 mg/kg, especially 0.2 to 10 mg/kg, per day.

Practical and presently-preferred embodiments of the present invention are illustratively shown in the following Examples. Throughout the specification and claims, the terms "lower alkyl" and "lower alkoxy" should be interpreted as referring to alkyl and alkoxy having one to four carbon atoms.

Experiments

Chemotherapeutic effects of the nitrosourea compounds of the invention on a variety of tumor cells in mice were investigated by the following methods and materials.

[METHODS]

(A) Preventive effect against the growth of Ehrlich ascites tumor $10^6$ tumor cells of Ehrlich ascites carcinoma were inoculated intraperitoneally into a group of five femal mice (ICR mice, body weight: 19–23 g). A test compound was dissolved in a physiological saline solution and administered intraperitoneally to the mice. The administration of the test compound was began 24 hours after the inoculation of the tumor cells and performed once a day for 5 days. The volume of ascites in the treated mice were measured after 7 days of the experiment.

(B) Effect on the life span of mice implanted with leukemic cells of L-1210

$10^5$ leukemic cells of L-1210 were inoculated intraperitoneally into a group of four male mice (BDF$_1$ mice, body weight: 19–23 g). A test compound was dissolved in a physiological saline solution and administered intraperitoneally to the mice. The administration of the test compound was began 24 hours after the inoculation of the leukemic cells and performed once a day for 5 days. The survival days of the treated mice were observed.

| Compound Nos. | [COMPOUNDS TESTED] Chemical Names |
|---|---|
| (The compounds of the present invention) | |
| 1. | 1-(2-chloroethyl)-1-nitroso-3-benzyl-3-[0-α-D-glucopyranosyl-(1→4)-D-glucopyranosyl]urea |
| 2. | 1-(2-chloroethyl)-1-nitroso-3-(p-methylbenzyl)-3-[0-α-D-glucopyranosyl-(1→4)-D-glucopyranosyl]urea |
| 3. | 1-(2-chloroethyl)-1-nitroso-3-(p-methoxybenzyl)-3-[0-α-D-glucopyranosyl-(1→4)-D-glucopyranosyl]urea |
| 4. | 1-(2-chloroethyl)-1-nitroso-3-phenethyl-3-[0-α-D-glucopyranosyl-(1→4)-D-glucopyranosyl]urea |
| 5. | 1-(2-chloroethyl)-1-nitroso-3-(α-methylbenzyl)-3-[0-α-D-glucopyranosyl-(1→4)-D-glucopyranosyl]urea |
| 6. | 1-(2-chloroethyl)-1-nitroso-3-furfuryl-3-[0-α-D-glucopyranosyl-(1→4)-D-glucopyranosyl]urea |
| 7. | 1-(2-chloroethyl)-1-nitroso-3-(thiophen-2-yl-methyl)-3-[0-α-D-glucopyranosyl-(1→4)-D-glucopyranosyl]urea |
| 8. | 1-(2-chloroethyl)-1-nitroso-3-cyclopropylmethyl-3-(D-galactopyranosyl)urea |
| 9. | 1-(2-chloroethyl)-1-nitroso-3-tetrahydrofurfuryl-3-(D-galactopyranosyl)urea |
| 10. | 1-(2-chloroethyl)-1-nitroso-3-cyclopropylmethyl-3-(L-arabinopyranosyl)urea |
| 11. | 1-(2-chloroethyl)-1-nitroso-3-benzyl-3-(L-arabinopyranosyl)urea |
| 12. | 1-(2-chloroethyl)-1-nitroso-3-(oxiran-2-yl-methyl)-3-(L-arabinopyranosyl)urea |
| 13. | 1-(2-chloroethyl)-1-nitroso-3-(thiophen-2-yl-methyl)-3-(L-arabinopyranosyl)urea |
| 14. | 1-(2-chloroethyl)-1-nitroso-3-furfuryl-3-(D-ribofuranosyl)urea |
| (Known compounds) | |
| CCNU | 1-(2-chloroethyl)-1-nitroso-3-cyclohexylurea |
| GANU | 1-(2-chloroethyl)-1-nitroso-3-(D-glucopyranosyl)-urea |

[RESULTS]

The results of the experiments are shown in the following Tables 1 and 2.

TABLE 1

Preventive effect against the growth of Ehrlich ascites carcinoma (Method A)

| Compound Nos. | Dose (mg/kg/day) | Ascites volume(g) T/C[a] | Inhibition ratio[b] (%) | MTD[c] | MED[d] | Therapeutic index[e] |
|---|---|---|---|---|---|---|
| | 800 | — | Toxic(5/5)* | | | |
| | 400 | 0.0/5.5 | 100 | | | |
| | 100 | 0.0/5.4 | 100 | | | |
| 1. | 25 | 0.0/5.4 | 100 | 400 | 1.56 | 256 |
| | 6.25 | 0.0/5.4 | 100 | | | |
| | 1.56 | 0.0/5.4 | 100 | | | |
| | 0.78 | 1.8/5.4 | 66.7 | | | |
| | 0.39 | 4.9/5.4 | 9.3 | | | |
| | 800 | — | Toxic(5/5)* | | | |
| | 400 | 0.0/3.9 | 100 | | | |
| | 100 | 0.0/3.9 | 100 | | | |
| 2. | 25 | 0.0/3.9 | 100 | 400 | 1.56 | 256 |

TABLE 1-continued

Preventive effect against the growth of Ehrlich ascites carcinoma (Method A)

| Compound Nos. | Dose (mg/kg/day) | Ascites volume(g) T/C[a] | Inhibition ratio[b] (%) | MTD[c] | MED[d] | Therapeutic index[e] |
|---|---|---|---|---|---|---|
| | 6.25 | 0.0/3.9 | 100 | | | |
| | 1.56 | 0.0/3.9 | 100 | | | |
| | 0.78 | 1.0/3.9 | 74.4 | | | |
| | 0.39 | 3.4/3.9 | 12.8 | | | |
| | 800 | — | Toxic(5/5)* | | | |
| | 400 | 0.0/3.9 | 100 | | | |
| | 100 | 0.0/3.9 | 100 | | | |
| 3. | 25 | 0.0/3.9 | 100 | 400 | 1.56 | 256 |
| | 6.25 | 0.0/3.9 | 100 | | | |
| | 1.56 | 0.0/3.9 | 100 | | | |
| | 0.78 | 3.0/3.9 | 23.1 | | | |
| | 400 | — | Toxic(5/5)* | | | |
| | 200 | 0.0/3.9 | 100 | | | |
| | 50 | 0.0/3.9 | 100 | | | |
| 4. | 12.5 | 0.0/3.9 | 100 | 200 | 3.12 | 64 |
| | 3.12 | 0.0/3.9 | 100 | | | |
| | 1.56 | 1.3/3.9 | 66.7 | | | |
| | 0.78 | 3.8/3.9 | 2.6 | | | |
| | 800 | — | Toxic(4/5)* | | | |
| | 400 | 0.0/4.8 | 100 | | | |
| | 100 | 0.0/4.8 | 100 | | | |
| 5. | 25 | 0.0/4.8 | 100 | 400 | 3.12 | 128 |
| | 6.25 | 0.0/4.8 | 100 | | | |
| | 3.12 | 0.0/4.8 | 100 | | | |
| | 1.56 | 4.5/4.8 | 6.2 | | | |
| | 800 | — | Toxic(5/5)* | | | |
| | 400 | 0.0/5.1 | 100 | | | |
| | 100 | 0.0/5.1 | 100 | | | |
| 6. | 25 | 0.0/5.1 | 100 | 400 | 3.12 | 128 |
| | 6.25 | 0.0/5.1 | 100 | | | |
| | 3.12 | 0.0/5.1 | 100 | | | |
| | 1.56 | 1.2/5.1 | 76.5 | | | |
| | 0.78 | 4.0/5.1 | 21.6 | | | |
| | 800 | — | Toxic(5/5)* | | | |
| | 400 | 0.0/4.8 | 100 | | | |
| | 100 | 0.0/4.8 | 100 | | | |
| 7. | 25 | 0.0/4.8 | 100 | 400 | 1.56 | 256 |
| | 6.25 | 0.0/4.8 | 100 | | | |
| | 1.56 | 0.0/4.8 | 100 | | | |
| | 0.78 | 3.3/4.8 | 31.2 | | | |
| | 0.39 | 4.5/4.8 | 6.2 | | | |
| | 200 | — | Toxic(3/5)* | | | |
| | 100 | 0.0/5.2 | 100 | | | |
| | 25 | 0.0/5.2 | 100 | | | |
| 8. | 6.25 | 0.0/5.2 | 100 | 100 | 0.78 | 128 |
| | 1.56 | 0.0/5.2 | 100 | | | |
| | 0.78 | 0.0/5.2 | 100 | | | |
| | 0.39 | 4.1/5.2 | 21.1 | | | |
| | 200 | — | Toxic(5/5)* | | | |
| | 100 | 0.0/4.8 | 100 | | | |
| | 25 | 0.0/4.8 | 100 | | | |
| 9. | 6.25 | 0.0/4.8 | 100 | 100 | 1.56 | 64 |
| | 1.56 | 0.0/4.8 | 100 | | | |
| | 0.78 | 3.0/4.8 | 37.5 | | | |
| | 0.39 | 4.5/4.8 | 6.2 | | | |
| | 200 | — | Toxic(5/5)* | | | |
| | 100 | 0.0/3.9 | 100 | | | |
| | 25 | 0.0/3.9 | 100 | | | |
| 10. | 6.25 | 0.0/3.9 | 100 | 100 | 0.78 | 128 |
| | 1.56 | 0.0/3.9 | 100 | | | |
| | 0.78 | 0.0/3.9 | 100 | | | |
| | 0.39 | 0.8/3.9 | 79.5 | | | |
| | 0.19 | 3.2/3.9 | 17.9 | | | |
| | 200 | — | Toxic(5/5)* | | | |
| | 100 | 0.0/4.9 | 100 | | | |
| | 25 | 0.0/4.9 | 100 | | | |
| 11. | 6.25 | 0.0/4.9 | 100 | 100 | 0.78 | 128 |
| | 1.56 | 0.0/4.9 | 100 | | | |
| | 0.78 | 0.0/4.9 | 100 | | | |
| | 0.39 | 1.7/4.9 | 65.3 | | | |
| | 0.19 | 4.0/4.9 | 18.4 | | | |
| | 100 | — | Toxic(5/5)* | | | |
| | 50 | 0.0/4.3 | 100 | | | |
| | 12.5 | 0.0/4.3 | 100 | | | |
| 12. | 3.12 | 0.0/4.3 | 100 | 50 | 0.39 | 128 |
| | 0.78 | 0.0/4.3 | 100 | | | |
| | 0.39 | 0.0/4.3 | 100 | | | |

TABLE 1-continued

Preventive effect against the growth of Ehrlich ascites carcinoma (Method A)

| Compound Nos. | Dose (mg/kg/day) | Ascites volume(g) T/C[a] | Inhibition ratio[b] (%) | MTD[c] | MED[d] | Therapeutic index[e] |
|---|---|---|---|---|---|---|
| | 0.19 | 3.4/4.3 | 20.9 | | | |
| | 200 | — | Toxic(5/5)* | | | |
| | 100 | 0.0/5.0 | 100 | | | |
| | 25 | 0.0/5.0 | 100 | | | |
| 13. | 6.25 | 0.0/5.0 | 100 | 100 | 0.78 | 128 |
| | 1.56 | 0.0/5.0 | 100 | | | |
| | 0.78 | 0.0/5.0 | 100 | | | |
| | 0.39 | 2.3/5.0 | 54.0 | | | |
| | 0.19 | 4.1/5.0 | 18.0 | | | |
| | 200 | — | Toxic(5/5)* | | | |
| | 100 | 0.0/4.9 | 100 | | | |
| | 25 | 0.0/4.9 | 100 | | | |
| 14 | 6.25 | 0.0/4.9 | 100 | 100 | 1.56 | 64 |
| | 1.56 | 0.0/4.9 | 100 | | | |
| | 0.78 | 3.4/4.9 | 30.6 | | | |
| | 0.39 | 4.0/4.9 | 18.4 | | | |
| | 100 | — | Toxic(5/5)* | | | |
| | 50 | 0.0/5.7 | 100 | | | |
| CCNU | 12.5 | 0.0/5.7 | 100 | 50 | 12.5 | 4 |
| | 6.25 | 3.8/5.7 | 33.3 | | | |
| | 3.12 | 4.5/5.7 | 21.1 | | | |
| | 25 | — | Toxic(5/5)* | | | |
| | 12.5 | 0.0/4.8 | 100 | | | |
| | 3.12 | 0.0/4.8 | 100 | | | |
| GANU | 0.78 | 0.0/4.8 | 100 | 12.5 | 0.39 | 32 |
| | 0.39 | 0.0/4.8 | 100 | | | |
| | 0.19 | 1.0/4.8 | 79.2 | | | |
| | 0.09 | 4.6/4.8 | 4.2 | | | |

Note:
[a]: T = the average volume of ascites in the treated mice
C = the average volume of ascites in the untreated mice (control group of mice)
[b]: Inhibition ratio (%) = $\frac{C-T}{C} \times 100$
[c]: MTD = Maximum Tolerated Dose (i.e., the maximum dose which shows 100% inhibition for the growth of Ehrlich ascites tumor in mice without causing the death of said mice)
[d]: MED = Minimum Effective Dose (i.e., the minimum dose which shows 100% inhibition for the growth of said ascites tumor)
[e]: Therapeutic index = MTD/MED
*: the number of mice died/the number of mice used

TABLE 2

Effect on life span of mice implanted with Leukemia L-1210 (Method B)

| Compound Nos. | Dose (mg/kg/day) | Survival days T/C[a] | ILS[b] (%) | 60-day survivors[c] |
|---|---|---|---|---|
| 1. | 200 | >60.0/8.7 | >589.7 | 4/4 |
| | 100 | >29.3/8.7 | >236.8 | 1/4 |
| | 25 | 13.5/8.7 | 55.2 | 0/4 |
| 3. | 400 | >60.0/7.3 | >721.9 | 4/4 |
| | 200 | >31.3/7.3 | >328.8 | 2/4 |
| | 25 | 11.0/7.3 | 50.7 | 0/4 |
| 6. | 200 | >60.0/7.2 | >733.3 | 4/4 |
| | 100 | >32.5/7.2 | >351.4 | 2/4 |
| | 25 | 11.9/7.2 | 65.3 | 0/4 |
| 8. | 50 | >60.0/8.0 | >650.0 | 4/4 |
| | 25 | >60.0/8.0 | >650.0 | 4/4 |
| | 6.25 | 12.3/8.0 | 53.8 | 0/4 |
| 9. | 100 | >60.0/7.6 | >689.5 | 4/4 |
| | 25 | >60.0/7.6 | >689.5 | 4/4 |
| | 6.25 | 11.8/7.6 | 55.3 | 0/4 |
| 10. | 50 | >60.0/7.3 | >721.9 | 4/4 |
| | 25 | >60.0/7.3 | >721.9 | 4/4 |
| | 6.25 | 13.3/7.3 | 82.2 | 0/4 |
| 13. | 50 | >36.0/7.0 | >414.3 | 2/4 |
| | 25 | >38.0/7.0 | >442.9 | 2/4 |
| | 12.5 | 15.5/7.0 | 121.4 | 0/4 |

Note:
[a]: T = the mean survival days of the treated mice
C = the mean survival days of the untreated mice (control group of mice)
[b]: ILS (Increase in Life Span) = $\frac{T-C}{C} \times 100$
[c]: 60-day survivors = the number of mice survived for 60 days/the number of mice used

EXAMPLE 1

(1) A mixture of 7.2 g of D-maltose monohydrate, 2.4 g of cyclopropylmethylamine and 20 ml of methanol is heated at 60° C. for one hour under stirring. After the reaction, the reaction mixture is condensed to dryness under reduced pressure, and the residue is washed with ether, whereby 7.8 g of [O-α-D-glucopyranosyl-(1→4)-D-glucopyranosyl]-cyclopropylmethylamine (i.e., 1-cyclopropylmethylamino-1-deoxy-D-maltose) are obtained as a crude product. 7.8 g of said crude product are dissolved in 50 ml of methanol, and a solution of 2.5 g of 2-chloroethyl isocyanate in 10 ml of tetrahydrofuran is added at 0° to 5° C. thereto. The solution is stirred at room temperature for 1.5 hours. Then, the reaction solution is condensed under reduced pressure, and a mixture of ethyl acetate and ether is added to the residue. 6.8 g of 1-(2-chloroethyl)-3-cyclopropylmethyl-3-[O-α-D-glucopyranosyl-(1→4)-D-glucopyranosyl]urea (i.e., 1-(2-chloroethyl)-3-cyclopropylmethyl-3-(D-maltosyl)urea) are thereby obtained as colorless amorphous powder IR $\nu_{max}^{Nujol}$ (cm$^{-1}$): 3350, 1640, 1535, 1070, 1030,
NMR (D$_2$O)δ: 0.30–0.70

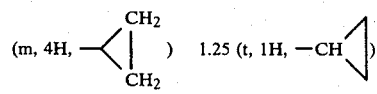

(2) 5.0 g of 1-(2-chloroethyl)-3-cyclopropylmethyl-3-[O-α-D-glucopyranosyl-(1→4)-D-glucopyranosyl]urea are dissolved in a mixture of 150 ml of tetrahydrofuran and 20 ml of acetic acid, and 20 g of sodium acetate anhydrate are added thereto. 8 g of nitrogen tetroxide gas are introduced into the mixture for 10 minutes under ice-cooling and stirring. The mixture is further stirred at the same temperature for 20 minutes. After the reaction, 200 ml of n-hexane are added to the mixture, and the mixture is filtered to remove insoluvle materials. The filtrate is evaporated to remove solvent. 200 ml of ether-methanol (20:1) are added to the residue, and the resultant oil is collected therefrom. Said oil is purified by silica gel chromatography (Solvent: ethyl acetate-chloroform-methanol (2:1:1)). 3.8 g of 1-(2-chloroethyl)-1-nitroso-3-cyclopropylmethyl-3-[O-α-D-glucopyranosyl-(1→4)-D-glucopyranosyl]urea (i.e., 1-(2-chloroethyl)-1-nitroso-3-cyclopropylmethyl-3-(D-maltosyl)urea) are thereby obtained as pale yellow powder.

M.p. 57° C. (decomp.)
IR$\nu_{max}^{Nujol}$ (cm$^{-1}$): 3300, 1690, 1080, 1030
NMR (D$_2$O)δ: 0.30–0.70

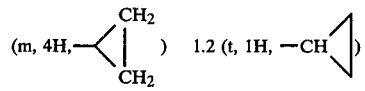

$[\alpha]_D^{20}+58.5°$ (C=1.5, methanol)

EXAMPLE 2

(1) 7.2 g of D-maltose monohydrate, 4.0 g of cyclohexylmethylamine and 2.5 g of 2-chloroethyl isocyanate are treated in the same manner as described in Example 1-(1). 7.2 g of 1-(2-chloroethyl)-3-cyclohexylmethyl-3-[O-α-D-glucopyranosyl-(1→4)-D-glucopyranosyl]urea (i.e., 1-(2-chloroethyl)-3-cyclohexylmethyl-3-(D-maltosyl)urea) are thereby obtained as colorless amorphous powder.

IR$\nu_{max}^{Nujol}$ (cm$^{-1}$): 3350, 1650, 1540, 1070,
NMR (D$_2$O) δ: 0.5–2.2 (m, cyclohexyl ring protons)

(2) 5.4 g of 1-(2-chloroethyl)-3-cyclohexylmethyl-3-[O-α-D-glucopyranosyl-(1→4)-D-glucopyranosyl]urea and 8 g of nitrogen tetroxide gas are treated in the same manner as described in Example 1-(2). 4.0 g of 1-(2-chloroethyl)-1-nitroso-3-cyclohexylmethyl-3-[O-α-D-glucopyranosyl-(1→4)-D-glucopyranosyl]urea (i.e., 1-(2-chloroethyl)-1-nitroso-3-cyclohexylmethyl-3-(D-maltosyl)urea are thereby obtained as pale yellow powder.

M.p. 68° C. (decomp.)
IR$\nu_{max}^{Nujol}$ (cm$^{-1}$): 3340, 1690, 1080, 1030,
NMR (D$_2$O) δ: 0.5–2.2 (m, cyclohexyl ring protons)
$[\alpha]_D^{22}+51.6°$ (C=1.2, methanol)

EXAMPLE 3

(1) 7.2 g of D-maltose monohydrate, 3.4 g of 2-cyclopentylethylamine and 2.5 g of 2-chloroethyl isocyanate are treated in the same manner as described in Example 1-(1). 7.8 g of 1-(2-chloroethyl)-3-(2-cyclopentylethyl)-3-[O-α-D-glucopyranosyl-(1→4)-D-glucopyranosyl]urea (i.e., 1-(2-chloroethyl)-3-(2-cyclopentylethyl)-3-(D-maltosyl)urea) are thereby obrtained as colorless amorphous powder.

IR$\nu_{max}^{Nujol}$ (cm$^{-1}$): 3350, 1630, 1540, 1070, 1040
NMR (D$_2$O) δ: 0.7–2.15

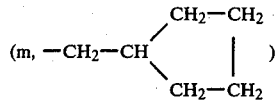

(2) 5.4 g of 1-(2-chloroethyl)-3-(2-cyclopentylethyl)-3-[O-α-D-glucopyranosyl-(1→4)-D-glucopyranosyl]urea and 8 g of nitrogen tetroxide gas are treated in the same manner as described in Example 1-(2). 4.2 g of 1-(2-chloroethyl)-1-nitroso-3-(2-cyclopentylethyl)-3-[O-α-D-glucopyranosyl-(1→4)-D-glucopyranosyl]urea (i.e., 1-(2-chloroethyl)-1-nitroso-3-(2-cyclopentylethyl)-3-(D-maltosyl)-urea) are thereby obtained as pale yellow powder.

M.p. 63° C. (decomp.)
IR$\nu_{max}^{Nujol}$ (cm$^{-1}$): 3360, 1690, 1050,
NMR (D$_2$O) δ: 0.7–2.1

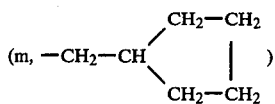

$[\alpha]_D^{10}+57.8°$ (C=1.2, methanol)

EXAMPLE 4

(1) 7.2 g of D-maltose monohydrate, 3.2 g of benzylamine and 3.0 g of 2-chloroethyl isocyanate are treated in the same manner as described in Example 1-(1). 6.9 g of 1-(2-chloroethyl)-3-benzyl-3-[O-α-D-glucopyranosyl-(1→4)-D-glucopyranosyl]urea (i.e., 1-(2-chloroethyl)-3-benzyl-3-(D-maltosyl)urea) are thereby obtained as colorless amorphous powder.

IR$\nu_{max}^{Nujol}$ (cm$^{-1}$): 3320, 1640, 1535, 1080, 1030,
NMR (D$_2$O) δ: 7.3–7.55 (m, phenyl protons)

(2) 5.4 g of 1-(2-chloroethyl)-3-benzyl-3-[O-α-D-glucopyranosyl-(1→4)-D-glucopyranosyl]urea and 8 g of nitrogen tetroxide gas are treated in the same manner as described in Example 1-(2). 3.7 g of 1-(2-chloroethyl)-1-nitroso-3-benzyl-3-[O-α-D-glucopyranosyl-(1→4)-D-glucopyranosyl]urea (i.e., 1-(2-chloroethyl)-1-nitroso-3-benzyl-3-(D-maltosyl)urea) are thereby obtained as pale yellow powder.

M.p. 70°–74° C. (decomp.)
IR$\nu_{max}^{Nujol}$ (cm$^{-1}$): 3300, 1690, 1080, 1030,
NMR (D$_2$O) δ: 7.2–7.6 (m, phenyl protons)
$[\alpha]_D^{20}+27.3°$ (C=1.0, methanol)

EXAMPLE 5

(1) 7.2 g of D-maltose monohydrate, 4.2 g of p-chlorobenzylamine and 3.0 g of 2-chloroethyl isocyanate are treated in the same manner as described in Example 1-(1). 6.3 g of 1-(2-chloroethyl)-3-(p-chlorobenzyl)-3-[O-α-D-glucopyranosyl-(1→4)-D-glucopyranosyl]urea (i.e., 1-(2-chloroethyl)-3-(p-chlorobenzyl)-3-(D-maltosyl)urea) are thereby obtained as colorless amorphous powder.

IR$\nu_{max}^{Nujol}$ (cm$^{-1}$): 3350, 1640, 1535, 1080, 1030,
NMR (D$_2$O) δ: 7.2–7.5 (m, phenyl protons)

(2) 5.7 g of 1-(2-chloroethyl)-3-(p-chlorobenzyl)-3-[O-α-D-glucopyranosyl-(1→4)-D-glucopyranosyl]urea and 8 g of nitrogen tetroxide gas are treated in the same manner as described in Example 1-(2). 4.0 g of 1-(2-chloroethyl)-1-nitroso-3-(p-chlorobenzyl)-3-[O-α-D-glucopyranosyl-(1→4)-D-glucopyranosyl]urea (i.e., 1-

(2-chloroethyl)-1-nitroso-3-(p-chlorobenzyl)-3-(D-maltosyl)urea) are thereby obtained as pale yellow powder.

M.p. 83° C. (decomp.)

IR$\nu_{max}^{Nujol}$ (cm$^{-1}$): 3300, 1690, 1050,

NMR (D$_2$O) δ: 7.5 (m, phenyl protons)

[α]$_D^{21}$ +16.6° (C=1.2, methanol)

EXAMPLE 6

(1) 7.2 g of D-maltose monohydrate, 4.1 g of p-methylbenzylamine and 3.0 g of 2-chloroethyl isocyanate are treated in the same manner as described in Example 1-(1). 7.0 g of 1-(2-chloroethyl)-3-(p-methylbenzyl)-3-[O-α-D-glucopyranosyl-(1→4)-D-glucopyranosyl]urea (i.e., 1-(2-chloroethyl)-3-(p-methylbenzyl)-3-(D-maltosyl)urea are thereby obtained as colorless amorphous powder.

IR$\nu_{max}^{Nujol}$ (cm$^{-1}$): 3350, 1640, 1535, 1070, 1030,

NMR (D$_2$O) δ: 2.30

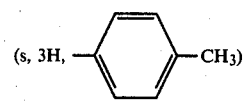
(s, 3H, —⬡—CH$_3$)

7.20 (q, 4 H, phenyl protons)

(2) 5.5 g of 1-(2-chloroethyl)-3-(p-methylbenzyl)-3-[O-α-D-glucopyranosyl-(1→4)-D-glucopyranosyl]urea and 8 g of nitrogen tetroxide gas are treated in the same manner as described in Example 1-(2). 4.0 g of 1-(2-chloroethyl)-1-nitroso-3-(p-methylbenzyl)-3-[O-α-D-glucopyranosyl-(1→4)-D-glucopyranosyl]urea (i.e., 1-(2-chloroethyl)-1-nitroso-3-(p-methylbenzyl)-3-(D-maltosyl)urea) are thereby obtained as pale yellow powder.

M.p. 86°-88° C. (decomp.)

IR$\nu_{max}^{Nujol}$ (cm$^{-1}$): 3350, 1690, 1070, 1020,

NMR (d$_6$-DMSO) δ: 2.25

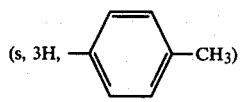
(s, 3H, —⬡—CH$_3$)

7.15 (q, 4 H, phenyl protons)

[α]$_D^{20}$ +29.5° (C=1.2, methanol)

EXAMPLE 7

(1) A mixture of 7.2 g of D-maltose monohydrate, 4.5 g of (2,4,6-trimethylbenzyl)amine and 20 ml of methanol is heated at 60° C. for one hour under stirring. After the reaction, the mixture is condensed to dryness under reduced pressure, and the residue is washed with ether, whereby 9.5 g of 1-[(2,4,6-trimethylbenzyl)amino]-1-deoxy-D-maltose are obtained as a crude product. 9.5 g of said crude product are dissolved in 50 ml of methanol, and a solution of 2.5 g of 2-chloroethyl isocyanate in 10 ml of tetrahydrofuran is added to 0° to 5° C. thereto. The solution is stirred at room temperature for 1.5 hours. Then, the reaction solution is condensed under reduced pressure, and the residue is purified by silica gel chromatography (Solvent: ethyl acetate-chloroform-methanol(1:1:1)). 8.0 g of 1-(2-chloroethyl)-3-(2,4,6-trimethylbenzyl)-3-[O-α-D-glucopyranosyl-(1→4)-D-glucopyranosyl]urea (i.e., 1-(2-chloroethyl)-3-(2,4,6-trimethylbenzyl)-3-(D-maltosyl)urea are thereby obtained as colorless powder.

IR$\nu_{max}^{Nujol}$ (cm$^{-1}$): 3310, 1610, 1530, 1070, 1030,

NMR (d$_6$-DMSO) δ: 2.24 (s, CH$_3$), 2.30 (s, CH$_3$), 6.88 (s, phenyl protons).

(2) 5.8 g of 1-(2-chloroethyl)-3-(2,4,6-trimethylbenzyl)-3-[O-α-D-glucopyranosyl-(1→4)-D-glucopyranosyl]urea are suspended in a mixture of 150 ml of tetrahydrofuran and 20 ml of acetic acid, and 20 g of sodium acetate anhydrate are added thereto. 8 g of nitrogen tetroxide gas are introduced into the mixture at −5° to 0° C. for 10 minutes under stirring. The mixture is further stirred at the same temperature for 20 minutes. 200 ml of n-hexane are added to the mixture, and insoluble materials are removed by filtration. The filtrate is evaporated to remove solvent. 200 ml of ether-methanol (20:1) are added to the residue, and the resultant oil is collected therefrom. Said oil is purified by silica gel chromatography (Solvent: ethyl acetate-chloroform-methanol (2:1:1)). 4.5 g of 1-(2-chloroethyl)-1-nitroso-3-(2,4,6-trimethylbenzyl)-3-[O-α-D-glucopyranosyl-(1→4)-D-glucopyranosyl]urea (i.e., 1-(2-chloroethyl)-1-nitroso-3-(2,4,6-trimethylbenzyl)-3-(D-maltosyl)urea) are thereby obtained as pale yellow powder.

M.p. 76°-80° C. (decomp.)

IR$\nu_{max}^{Nujol}$ (cm$^{-1}$): 3375, 1695, 1070, 1030,

NMR (D$_2$O) δ: 2,15 (s, CH$_3$), 2.12 (s, CH$_3$), 6.75 (s, phenyl protons).

[α]$_D^{28}$ +12.0° (C=1.0, methanol)

EXAMPLE 8

(1) 7.2 g of D-maltose monohydrate, 4.1 g of p-methoxybenzylamine and 3.0 g of 2-chloroethyl isocyanate are treated in the same manner as described in Example 1-(1). 7.4 g of 1-(2-chloroethyl)-3-(p-methoxybenzyl)-3-[O-α-D-glucopyranosyl-(1→4)-D-glucopyranosyl]urea (i.e., 1-(2-chloroethyl)-3-(p-methoxybenzyl)-3-(D-maltosyl)urea are thereby obtained as colorless amorphous powder.

IR$\nu_{max}^{Nujol}$ (cm$^{-1}$): 3320, 1640, 1530, 1080, 1030,

NMR (D$_2$O) δ: 3.80,

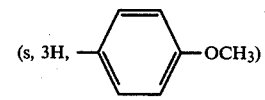
(s, 3H, —⬡—OCH$_3$)

7.20 (q, 4 H, phenyl protons)

(2) 5.7 g of 1-(2-chloroethyl)-3-(p-methoxybenzyl)-3-[O-α-D-glucopyranosyl-(1→4)-D-glucopyranosyl]urea and 8 g of nitrogen tetroxide gas are treated in the same manner as described in Example 1-(2). 4.1 g of 1-(2-chloroethyl)-1-nitroso-3-(p-methoxybenzyl)-3-[O-α-D-glucopyranosyl-(1→4)-D-glucopyranosyl]urea (i.e., 1-(2-chloroethyl)-1-nitroso-3-(p-methoxybenzyl)-3-(D-maltosyl)urea) are thereby obtained as pale yellow powder.

M.p. 83°-86° C. (decomp.)

IR$\nu_{max}^{Nujol}$ (cm$^{-1}$): 3350, 1690, 1070, 1030,

NMR (d$_6$-DMSO) δ: 3.75

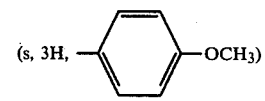
(s, 3H, —⬡—OCH$_3$)

7.15 (q, 4 H, phenyl protons)

[α]$_D^{18}$ +29.2° (C=1.1, methanol)

EXAMPLE 9

(1) 7.2 g of D-maltose monohydrate, 4.2 g of (2,3-dimethoxybenzyl)amine and 2.5 g of 2-chloroethyl isocyanate are treated in the same manner as described in Example 7-(1). 8.1 g of 1-(2-chloroethyl)-3-(2,3-dimethoxybenzyl)-3-[O-α-D-glucopyranosyl-(1→4)-D-glucopyranosyl]urea (i.e., 1-(2-chloroethyl)-3-(2,3-dimethoxybenzyl)-3-(D-maltosyl)urea) are thereby obtained as colorless caramel.

IR$\nu_{max}^{Nujol}$ (cm$^{-1}$): 3350, 1635, 1530, 1070, 1020,

NMR (D$_2$O) δ: 3.8 (s, OC$\underline{H}_3$), 6.9–7.2 (m, phenyl protons).

(2) 6.0 g of 1-(2-chloroethyl)-3-(2,3-dimethoxybenzyl)-3-[O-α-D-glucopyranosyl-(1→4)-D-glucopyranosyl]urea and 8.0 g of nitrogen tetroxide gas are treated in the same manner as described in Example 7-(2). 3.6 g of 1-(2-chloroethyl)-1-nitroso-3-(2,3-dimethoxybenzyl)-3-[O-α-D-glucopyranosyl-(1→4)-D-glucopyranosyl]urea (i.e., 1-(2-chloroethyl)-1-nitroso-3-(2,3-dimethoxybenzyl)-3-(D-maltosyl)-urea) are thereby obtained as pale yellow powder.

M.p. 62°–68° C. (decomp.)

IR$\nu_{max}^{Nujol}$ (cm$^{-1}$): 3375, 1705, 1070,

NMR (D$_2$O) δ: 3.8 (s, OC$\underline{H}_3$), 6.9–7.2 (m, phenyl protons).

$[\alpha]_D^{28}$ +32.1° (C=1.0, methanol)

EXAMPLE 10

(1) 7.2 g of D-maltose monohydrate, 8.0 g of (3,4,5-trimethoxybenzyl)amine and 2.5 g of 2-chloroethyl isocyanate are treated in the same manner as described in Example 7-(1). 9.5 g of 1-(2-chloroethyl)-3-(3,4,5-trimethoxybenzyl)-3-[O-α-D-glucopyranosyl-(1→4)-D-glucopyranosyl]urea (i.e., 1-(2-chloroethyl)-3-(3,4,5-trimethoxybenzyl)-3-(D-maltosyl)urea) are thereby obtained as colorless powder.

IR$\nu_{max}^{Nujol}$ (cm$^{-1}$): 3370, 1640, 1595, 1505, 1120, 1070, 1025,

NMR (D$_2$O) δ: 3.86 (s, 9 H, OC$\underline{H}_3$), 6.83 (s, 2 H, phenyl protons).

(2) 5.2 g of 1-(2-chloroethyl)-3-(3,4,5-trimethoxybenzyl)-3-[O-α-D-glucopyranosyl-(1→4)-D-glucopyranosyl]urea and 8.0 g of nitrogen tetroxide gas are treated in the same manner as described in Example 7-(2). 4.0 g of 1-(2-chloroethyl)-1-nitroso-3-(3,4,5-trimethoxybenzyl)-3-[O-α-D-glucopyranosyl-(1→4)-D-glucopyranosyl]urea (i.e., 1-(2-chloroethyl)-1-nitroso-3-(3,4,5-trimethoxybenzyl)-3-(D-maltosyl)urea) are thereby obtained as pale yellow powder.

M.p. 98° C. (decomp.)

IR$\nu_{max}^{Nujol}$ (cm$^{-1}$): 3380, 1695, 1590, 1500, 1125, 1070, 1050, 1030, NMR (D$_2$O) δ: 3.82 (s, 9 H, OC$\underline{H}_3$), 6.75 (s, 2 H, phenyl protons).

$[\alpha]_D^{22}$ +23.2° (C=1.0, methanol).

EXAMPLE 11

(1) 7.2 g of D-maltose monohydrate, 3.0 g of (p-hydroxybenzyl)amine and 2.5 g of 2-chloroethyl isocyanate are treated in the same manner as described in Example 7-(1). 5.7 g of 1-(2-chloroethyl)-3-(p-hydroxybenzyl)-3-[O-α-D-glucopyranosyl-(1→4)-D-glucopyranosyl]urea (i.e., 1-(2-chloroethyl)-3-(p-hydroxybenzyl)-3-(D-maltosyl)urea) are thereby obtained as colorless caramel.

IR$\nu_{max}^{Nujol}$ (cm$^{-1}$): 3360, 1630, 1610, 1510, 1070, 1020,

NMR (D$_2$O) δ: 6.82 (d, 2 H, phenyl protons), 7.22 (d, 2 H, phenyl protons).

(2) 5.5 g of 1-(2-chloroethyl)-3-(p-hydroxybenzyl)-3-[O-α-D-glucopyranosyl-(1→4)-D-glucopyranosyl]urea and 8.0 g of nitrogen tetroxide gas are treated in the same manner as described in Example 7-(2). 2.4 g of 1-(2-chloroethyl)-1-nitroso-3-(p-hydroxybenzyl)-3-[O-α-D-glucopyranosyl-(1→4)-D-glucopyranosyl]urea (i.e., 1-(2-chloroethyl)-1-nitroso-3-(p-hydroxybenzyl)-3-(D-maltosyl)urea) are thereby obtained as pale yellow powder.

M.p. 74° C. (decomp.)

IR$\nu_{max}^{Nujol}$ (cm$^{-1}$): 3360, 1700, 1070, 1050, 1025,

NMR (D$_2$O) δ: 7.04 (d, 2 H, phenyl protons), 7.56 (d, 2 H, phenyl protons).

$[\alpha]_D^{27}$ +47.6° (C=1.0, methanol).

EXAMPLE 12

(1) 7.2 g of D-maltose monohydrate, 4.5 g of (p-nitrobenzyl)amine and 2.5 g of 2-chloroethyl isocyanate are treated in the same manner as described in Example 7-(1). 8.0 g of 1-(2-chloroethyl)-3-(p-nitrobenzyl)-3-[O-α-D-glucopyranosyl-(1→4)-D-glucopyranosyl]urea (i.e., 1-(2-chloroethyl)-3-(p-nitrobenzyl)-3-(D-maltosyl)urea) are thereby obtained as pale yellow powder.

IR$\nu_{max}^{Nujol}$ (cm$^{-1}$): 3350, 1640, 1600, 1515, 1345, 1070, 1025,

NMR (D$_2$O) δ: 7.58 (d, 2 H, phenyl protons), 8.14 (d, 2 H, phenyl protons).

(2) 5.8 g of 1-(2-chloroethyl)-3-(p-nitrobenzyl)-3-[O-α-D-glucopyranosyl-(1→4)-D-glucopyranosyl]urea and 8.0 g of nitrogen tetroxide gas are treated in the same manner as described in Example 7-(2). 3.8 g of 1-(2-chloroethyl)-1-nitroso-3-(p-nitrobenzyl)-3-[O-α-D-glucopyranosyl-(1→4)-D-glucopyranosyl]urea (i.e., 1-(2-chloroethyl)-1-nitroso-3-(p-nitrobenzyl)-3-(D-maltosyl)urea) are thereby obtained as yellow powder.

M.p. 87°–89° C. (decomp.)

IR$\nu_{max}^{Nujol}$ (cm$^{-1}$): 3370, 1700, 1600, 1515, 1345, 1070, 1050, 1030, NMR (D$_2$O) δ: 7.44 (d, 2 H, phenyl protons) 7.90 (d, 2 H, phenyl protons).

$[\alpha]_D^{26}$ +10.5° (C=1.0, methanol).

EXAMPLE 13

(1) 7.2 g of D-maltose monohydrate, 3.2 g of phenethylamine and 3.0 g of 2-chloroethyl isocyanate are treated in the same manner as described in Example 1-(1). 7.1 g of 1-(2-chloroethyl)-3-phenethyl-3-[O-α-D-glucopyranosyl-(1→4)-D-glucopyranosyl]urea (i.e., 1-(2-chloroethyl)-3-phenethyl-3-(D-maltosyl)urea) are thereby obtained as colorless amorphous powder. p IR$\nu_{max}^{Nujol}$ (cm$^{-1}$): 3330, 1640, 1530, 1070, 1020, NMR (D$_2$O) δ: 7.3 (broad s, phenyl protons).

(2) 5.3 g of 1-(2-chloroethyl)-3-phenethyl-3-[O-α-D-glucopyranosyl-(1→4)-D-glucopyranosyl]urea and 8 g of nitrogen tetroxide gas are treated in the same manner as described in Example 1-(2). 3.8 g of 1-(2-chloroethyl)-1-nitroso-3-phenethyl-3-[O-α-D-glucopyranosyl-(1→4)-D-glucopyranosyl]urea (i.e., 1-(2-chloroethyl)-1-nitroso-3-phenethyl-3-(D-maltosyl)urea) are thereby obtained as pale yellow powder.

M.p. 72°–75° C. (decomp.)

IR$\nu_{max}^{Nujol}$ (cm$^{-1}$): 3350, 1690, 1070, 1020, $[\alpha]_D^{20}$ +58.6° (C=1.1, methanol), $[\alpha]_D^{20}$ +58.6° (C=1.1, methanol).

EXAMPLE 14

(1) 7.2 g of D-maltose monohydrate, 4.0 g of α-methylbenzylamine and 2.5 g of 2-chloroethyl isocyanate are treated in the same manner as described in Example 7-(1). 8.8 g of 1-(2-chloroethyl)-3-(α-methylbenzyl)-3-[O-α-D-glucopyranosyl-(1→4)-D-glucopyranosyl]urea (i.e., 1-(2-chloroethyl)-3-(α-methylbenzyl)-3-(D-maltosyl)urea) are thereby obtained as colorless caramel.

IR$\nu_{max}^{Nujol}$ (cm$^{-1}$): 3350, 1630, 1525, 1070, 1030.

NMR (d$_6$-DMSO) δ: 1.2–1.8 (m, 3H, C$\underline{H}_3$), 7.3 (s, 5H, phenyl protons).

(2) 5.5 g of 1-(2-chloroethyl)-3-(α-methylbenzyl)-3-[O-α-D-glucopyranosyl-(1→4)-D-glucopyranosyl]urea and 8.0 g of nitrogen tetroxide gas are treated in the same manner as described in Example 7-(2). 3.8 g of 1-(2-chloroethyl)-1-nitroso-3-(α-methylbenzyl)-3-[O-α-D-glucopyranosyl-(1→4)-D-glucopyranosyl]urea (i.e., 1-(2-chloroethyl)-1-nitroso-3-(α-methylbenzyl)-3-(D-maltosyl)urea) are thereby obtained as pale yellow powder.

M.p. 110° C. (decomp.).

IR$\nu_{max}^{Nujol}$ (cm$^{-1}$): 3380, 1690, 1070, 1030.

NMR (D$_2$O) δ: 1.50–1.84 (m, 3H, C$\underline{H}_3$), 7.04–7.56 (m, 5H, phenyl protons).

$[\alpha]_D^{26}$ +45.5° (C=1.1, methanol).

EXAMPLE 15

(1) 7.2 g of D-maltose monohydrate, 3.6 g of tetrahydrofurfurylamine and 2.5 g of 2-chloroethyl isocyanate are treated in the same manner as described in Example 1-(1). 7.5 g of 1-(2-chloroethyl)-3-tetrahydrofurfuryl-3-[O-α-D-glucopyranosyl-(1→4)-D-glucopyranosyl]urea (i.e., 1-(2-chloroethyl)-3-tetrahydrofurfuryl-3-(D-maltosyl)urea) are thereby obtained as colorless amorphous powder.

IR$\nu_{max}^{Nujol}$ (cm$^{-1}$): 3370, 1640, 1540, 1070.

NMR (D$_2$O) δ: 1.75–2.25

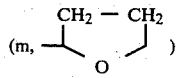

(2) 5.3 g of 1-(2-chloroethyl)-3-tetrahydrofurfuryl-3-[O-α-D-glucopyranosyl-(1→4)-D-glucopyranosyl]urea and 8 g of nitrogen tetroxide gas are treated in the same manner as described in Example 1-(2). 4.1 g of 1-(2-chloroethyl)-1-nitroso-3-tetrahydrofurfuryl-3-[O-α-D-glucopyranosyl-(1→4)-D-glucopyranosyl]urea (i.e., 1-(2-chloroethyl)-1-nitroso-3-tetrahydrofurfuryl-3-(D-maltosyl)urea) are thereby obtained as pale yellow powder.

M.p. 69°–71° C. (decomp.).

IR$\nu_{max}^{Nujol}$ (cm$^{-1}$): 3350, 1700, 1060.

NMR (D$_2$O) δ: 1.7–2.2

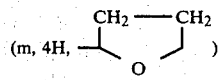

4.20 (t, 2H, —N(NO)—C$\underline{H}_2$—)

$[\alpha]_D^{20}$ +52.5° (C=1.2, methanol).

EXAMPLE 16

(1) 7.2 g of D-maltose monohydrate, 2.5 g of (1,3-dioxolan-4-yl-methyl)amine (obtained by catalytic hydrogenation of (1,3-dioxolan-4-yl-methyl)azide) and 2.5 g of 2-chloroethyl isocyanate are treated in the same manner as described in Example 7-(1). 5.8 g of 1-(2-chloroethyl)-3-(1,3-dioxolan-4-yl-methyl)-3-[O-α-D-glucopyranosyl-(1→4)-D-glucopyranosyl]urea (i.e., 1-(2-chloroethyl)-3-(1,3-dioxolan-4-yl-methyl)-3-(D-maltosyl)urea) are thereby obtained as colorless powder.

IR$\nu_{max}^{Nujol}$ (cm$^{-1}$): 3350, 1640, 1540, 1150, 1080, 1030.

(2) 5.3 g of 1-(2-chloroethyl)-3-(1,3-dioxolan-4-yl-methyl)-3-[O-α-D-glucopyranosyl-(1→4)-D-glucopyranosyl]urea and 8 g of nitrogen tetroxide gas are treated in the same manner as described in Example 7-(2). 3.6 g of 1-(2-chloroethyl)-1-nitroso-3-(1,3-dioxolan-4-yl-methyl)-3-[O-α-D-glucopyranosyl-(1→4)-D-glucopyranosyl]urea (i.e., 1-(2-chloroethyl)-1-nitroso-3-(1,3-dioxolan-4-yl-methyl)-3-(D-maltosyl)urea) are thereby obtained as pale yellow powder.

M.p. 62°–64° C. (decomp.).

IR$\nu_{max}^{Nujol}$ (cm$^{-1}$): 3350, 1700, 1150, 1080, 1030.

NMR (D$_2$O) δ: 4.20 (t, —N(NO)C$\underline{H}_2$—).

$[\alpha]_D^{26}$ +48.6° (C=1.2, methanol).

EXAMPLE 17

(1) 7.2 g of D-maltose monohydrate, 2.5 g of (1,3-dioxolan-2-yl-methyl)amine and 2.5 g of 2-chloroethyl isocyanate are treated in the same manner as described in Example 7-(1). 6.5 g of 1-(2-chloroethyl)-3-(1,3-dioxolan-2-yl-methyl)-3-[O-α-D-glucopyranosyl-(1→4)-D-glucopyranosyl]urea (i.e., 1-(2-chloroethyl)-3-(1,3-dioxolan-2-yl-methyl)-3-(D-maltosyl)urea) are thereby obtained as colorless caramel.

IR$\nu_{max}^{Nujol}$ (cm$^{-1}$): 3350, 1650, 1540, 1070, 1020.

(2) 5.3 g of 1-(2-chloroethyl)-3-(1,3-dioxolan-2-yl-methyl)-3-[O-α-D-glucopyranosyl-(1→4)-D-glucopyranosyl]urea and 8 g of nitrogen tetroxide gas are treated in the same manner as described in Example 7-(2). 3.2 g of 1-(2-chloroethyl)-1-nitroso-3-(1,3-dioxolan-2-yl-methyl)-3-[O-α-D-glucopyranosyl-(1→4)-D-glucopyranosyl]urea (i.e., 1-(2-chloroethyl)-1-nitroso-3-(1,3-dioxolan-2-yl-methyl)-3-(D-maltosyl)urea) are thereby obtained as pale yellow powder.

M.p. 85°–90° C. (decomp.).

IR$\nu_{max}^{Nujol}$ (cm$^{-1}$): 3375, 1700, 1040.

$[\alpha]_D^{27}$ +52.8° (C=1.0, methanol).

EXAMPLE 18

(1) 7.2 g of D-maltose monohydrate, 2.5 g of (1,4-dioxan-2-yl-methyl)amine and 2.5 g of 2-chloroethyl isocyanate are treated in the same manner as described in Example 7-(1). 6.3 g of 1-(2-chloroethyl)-3-(1,4-dioxan-2-yl-methyl)-3-[O-α-D-glucopyranosyl-(1→4)-D-glucopyranosyl]urea (i.e., 1-(2-chloroethyl)-3-(1,4-dioxan-2-yl-methyl)-3-(D-maltosyl)urea) are thereby obtained as colorless caramel.

IR$\nu_{max}^{Nujol}$ (cm$^{-1}$): 3350, 1640, 1540, 1120, 1080, 1030.

(2) 5.4 g of 1-(2-chloroethyl)-3-(1,4-dioxan-2-yl-methyl)-3-[O-α-D-glucopyranosyl-(1→4)-D-glucopyranosyl]urea and 8 g of nitrogen tetroxide gas are treated in the same manner as described in Example 7-(2). 3.6 g of 1-(2-chloroethyl)-1-nitroso-3-(1,4-dioxan-2-yl-methyl)-3-[O-α-D-glucopyranosyl-(1→4)-D-glucopyranosyl]urea (i.e., 1-(2-chloroethyl)-1-nitroso-3-(1,4-dioxan-2-yl-methyl)-3-(D-maltosyl)urea) are thereby obtained as pale yellow powder.

M.p. 74°–77° C. (decomp).

IR$\nu_{max}^{Nujol}$ (cm$^{-1}$): 3350, 1700, 1120, 1080, 1040.

$[\alpha]_D^{27}$ +43.8° (C=1.0, methanol).

EXAMPLE 19

(1) 7.2 g of D-maltose monohydrate, 3.6 g of tetrahydro-S,S-dioxo-3-thienylmethylamine (see; C. S. Argyle et al., J.Chem.Soc., 2156(1967)) and 2.5 g of 2-chloroethyl isocyanate are treated in the same manner as described in Example 1-(1). 6.4 g of 1-(2-chloroethyl)-3-(tetrahydro-S,S-dioxo-3-thienylmethyl)-3-[O-α-D-glucopyranosyl-(1→4)-D-glucopyranosyl]urea (i.e., 1-(2-chloroethyl)-3-(tetrahydro-S,S-dioxo-3-thienylmethyl)-3-(D-maltosyl)urea) are thereby obtained as colorless amorphous powder.

IR$\nu_{max}^{Nujol}$ (cm$^{-1}$): 3350, 1630, 1540, 1300, 1120, 1080, 1040.

(2) 5.8 g of 1-(2-chloroethyl)-3-(tetrahydro-S,S-dioxo-3-thienylmethyl)-3-[O-α-D-glucopyranosyl-(1→4)-D-glucopyranosyl]urea and 8 g of nitrogen tetroxide gas are treated in the same manner as described in Example 1-(2). 3.9 g of 1-(2-chloroethyl)-1-nitroso-3-(tetrahydro-S,S-dioxo-3-thienylmethyl)-3-[O-α-D-glucopyranosyl-(1→4)-D-glucopyranosyl]urea (i.e., 1-(2-chloroethyl)-1-nitroso-3-tetrahydro-S,S-dioxo-3-thienylmethyl)-3-(D-maltosyl)urea) are thereby obtained as pale yellow powder.

M.p. 74°-77° C. (decomp.).

IR$\nu_{max}^{Nujol}$ (cm$^{-1}$): 3350, 1700, 1300, 1120, 1080, 1030.

$[\alpha]_D$ +42.0° (C=1.6, methanol).

EXAMPLE 20

(1) 7.2 g of D-maltose monohydrate, 5.8 g of furfurylamine and 4.0 g of 2-chloroethyl isocyanate are treated in the same manner as described in Example 1-(1). 6.4 g of 1-(2-chloroethyl)-3-furfuryl-3-[O-α-D-glucopyranosyl-(1→4)-D-glucopyranosyl]urea (i.e., 1-(2-chloroethyl)-3-furfuryl-3-(D-maltosyl)urea) are thereby obtained as colorless amorphous powder.

M.p 103° C. (decomp.).

IR$\nu_{max}^{Nujol}$ (cm$^{-1}$): 3350, 1640, 1530, 1070, 1030.

NMR (D$_2$O) δ: 6.46 (m, 2H, furan ring protons), 7.53 (m, 2H, furan ring protons).

(2) 5.3 g of 1-(2-chloroethyl)-3-furfuryl-3-[O-α-D-glucopyranosyl-(1→4)-D-glucopyranosyl]urea and 8 g of nitrogen tetroxide gas are treated in the same manner as described in Example 1-(2). 3.9 g of 1-(2-chloroethyl)-1-nitroso-3-furfuryl-3-[O-α-D-glucopyranosyl-(1→4)-D-glucopyranosyl]urea (i.e., 1-(2-chloroethyl)-1-nitroso-3-furfuryl-3-(D-maltosyl)urea) are thereby obtained as pale yellow powder.

M.p. 54° C. (decomp.).

IR$\nu_{max}^{Nujol}$ (cm$^{-1}$): 3350, 1705, 1080, 1030.

NMR (D$_2$O) δ: 6.43 (m, 2H, furan ring protons), 7.45 (m, 1H, furan ring proton).

$[\alpha]_D^{15}$ +27.5 (C=1.0, methanol).

EXAMPLE 21

(1) 7.2 g of D-maltose monohydrate, 2.7 g of (thiophen-2-yl-methyl)amine and 2.5 g of 2-chloroethyl isocyanate are treated in the same manner as described in Example 7-(1). 7.6 g of 1-(2-chloroethyl)-3-(thiophen-2-yl-methyl)-3-[O-α-D-glucopyranosyl-(1→4)-D-glucopyranosyl]urea (i.e., 1-(2-chloroethyl)-3-(thiophen-2-yl-methyl)-3-(D-maltosyl)urea) are thereby obtained as colorless caramel.

IR$\nu_{max}^{Nujol}$ (cm$^{-1}$): 3340, 1620, 1530, 1070, 1020.

NMR (D$_2$O) δ: 6.9–7.2

7.3–7.5 (m, 2H, 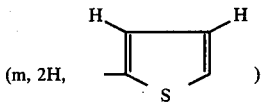 )

(m, 1H, 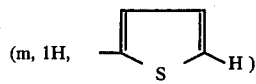 )

(2) 5.4 g of 1-(2-chloroethyl)-3-(thiophen-2-yl-methyl)-3-[O-α-D-glucopyranosyl-(1→4)-D-glucopyranosyl]urea and 8.0 g of nitrogen tetroxide gas are treated in the same manner as described in Example 7-(2). 3.2 g of 1-(2-chloroethyl)-1-nitroso-3-(thiophen-2-yl-methyl)-3-[O-α-D-glucopyranosyl-(1→4)-D-glucopyranosyl]urea (i.e., 1-(2-chloroethyl)-1-nitroso-3-(thiophen-2-yl-methyl)-3-(D-maltosyl)urea) are thereby obtained as pale yellow powder.

M.p. 60°-65° C. (decomp.).

IR$\nu_{max}^{Nujol}$ (cm$^{-1}$): 3375, 1700, 1070.

NMR (D$_2$O) δ: 6.9–7.2

7.3–7.5 (m, 2H, 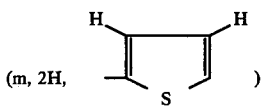 )

(m, 1H, 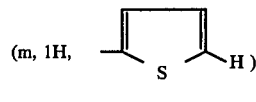 )

$[\alpha]_D^{24}$ +48.0° (C=1.0, methanol).

EXAMPLE 22

7.2 g of D-maltose monohydrate, 3.2 g of 4-pyridylmethylamine and 3.0 g of 2-chloroethyl isocyanate are treated in the same manner as described in Example 1-(1). 6.2 g of 1-(2-chloroethyl)-3-(4-pyridylmethyl)-3-[O-α-D-glucopyranosyl-(1→4)-D-glucopyranosyl]urea (i.e., 1-(2-chloroethyl)-3-(4-pyridylmethyl)-3-(D-maltosyl)urea) are thereby obtained as colorless caramel.

IR$\nu_{max}^{Nujol}$ (cm$^{-1}$): 3330, 1640, 1530, 1080, 1030.

NMR (d$_6$-DMSO) δ: 7.50 (m, 2H, pyridine ring protons), 8.50 (m, 2H, pyridine ring protons).

(2) 5.4 g of 1-(2-chloroethyl)-3-(4-pyridylmethyl)-3-[O-α-D-glucopyranosyl-(1→4)-D-glucopyranosyl]urea and 8 g of nitrogen tetroxide gas are treated in the same manner as described in Example 1-(2). 5.1 g of 1-(2-chloroethyl)-1-nitroso-3-(4-pyridylmethyl)-3-[O-α-D-glucopyranosyl-(1→4)-D-glucopyranosyl]urea (i.e., 1-(2-chloroethyl)-1-nitroso-3-(4-pyridylmethyl)-3-(D-maltosyl)urea) are thereby obtained as pale yellow powder.

M.p. 75°-78° C. (decomp.).

IR$\nu_{max}^{Nujol}$ (cm$^{-1}$): 3300, 1700, 1070, 1040.

NMR (d$_6$-DMSO) δ: 7.50 (m, 2H, pyridine ring protons), 8.55 (m, 2H, pyridine ring protons).

$[\alpha]_D^{18}$ +40.1° (C=0.8, methanol).

EXAMPLE 23

(1) A mixture of 3.6 g of D-galactose, 10 g of cyclohexylamine and 20 ml of methanol is heated at 60° C. for one hour under stirring. After the reaction, the reaction mixture is condensed to dryness under reduced pressure and the residue is washed with ether, whereby 5.2 g of 1-cyclohexylamino-b 1-deoxy-D-galactose are obtained as a crude product. 5.2 g of said crude product are dissolved in 50 ml of methanol, and a solution of 2.3 g of 2-chloroethyl isocyanate in 10 ml of tetrahydrofuran is added dropwise thereto at 0° to 5° C. The solution is stirred at room temperature for one hour. Then, the reaction solution is condensed under reduced pressure, and the residue obtained is dissolved in 20 ml of formic acid. The formic acid solution is allowed to stand at room temperature for 20 minutes, and 150 ml of ether-n-hexane (3:1) are added thereto. The resultant oil is purified by silica gel chromatography (Solvent:chloroform-ethyl acetatemethanol (3:1:1)). 3.2 g of 1-(2-chloroethyl)-3-cyclohexyl-3-(D-galactopyranosyl)urea are thereby obtained as colorless caramel.

IR$\nu_{max}^{Nujol}$ (cm$^{-1}$): 3360, 1630, 1540, 1060.
NMR (D$_2$O): δ: 1.0–2.0

(m, 10H, 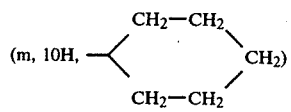)

(2) 3.7 g of 1-(2-chloroethyl)-3-cyclohexyl-3-(D-galactopyranosyl) urea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling and stirring. The mixture is further stirred at the same temperature for 10 minutes. After the reaction, 10 ml of methanol and 3 ml of water are added to the mixture, and the aqueous mixture is stirred vigorously for 10 minutes. Said aqueous mixture is dried and filtered. The filtrate is evaporated to remove solvent. Then, the residue obtained is purified by silica gel chromatography (Solvent: ethyl acetate-chloroform-methanol (5:2:1)). 2.8 g of 1-(2-chloroethyl)-1-nitroso-3-cyclohexyl-3-(D-galactopyranosyl)urea are thereby obtained as yellow caramel.

IR$\nu_{max}^{CHCl_3}$ (cm$^{-1}$): 3400, 1690, 1060.
NMR (D$_2$O) δ: 0.9–2.2

(m, 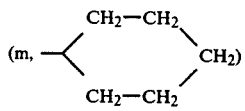)

$[\alpha]_D^{20}$ +21.6° (C=1.3, methanol).

EXAMPLE 24

(1) 3.6 g of D-galactose, 2.2 g of cyclopropylmethylamine and 2.5 g of 2-chloroethyl isocyanate are treated in the same manner as described in Example 23-(1). 4.5 g of 1-(2-chloroethyl)-3-cyclopropylmethyl-3-(D-galactopyranosyl)urea are thereby obtained as colorless caramel.

IR$\nu_{max}^{Nujol}$ (cm$^{-1}$): 3350, 1640, 1545, 1060.
NMR (D$_2$O) δ: 0.35–0.75

(m, 4H, 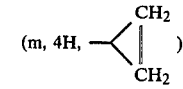)

1.1–1.5

(m, 1H, 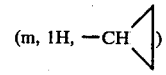)

(2) 3.4 g of 1-(2-chloroethyl)-3-cyclopropylmethyl-3-(D-galactopyranosyl)urea and 5 g of nitrogen tetroxide gas are treated in the same manner as described in Example 23-(2). 2.6 g of 1-(2-chloroethyl)-1-nitroso-3-cyclopropylmethyl-3-(D-galactopyranosyl)urea are obtained as yellow caramel.

IR$\nu_{max}^{CHCl_3}$ (cm$^{-1}$): 3380, 1690, 1090.
NMR (D$_2$O) δ: 0.3–0.7

(m, 4H, 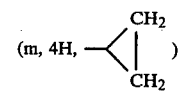)

1.0–1.4

(m, 1H, 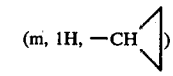)

$[\alpha]_D^{15}$ +18.6° (C=1.34, methanol).

EXAMPLE 25

(1) 3.6 g of D-galactose, 4.5 g of cyclohexylmethylamine and 2.5 g of 2-chloroethyl isocyanate are treated in the same manner as described in Example 23-(1). 4.7 g of 1-(2-chloroethyl)-3-cyclohexylmethyl-3-(D-galactopyranosyl)urea are thereby obtained as colorless caramel.

IR$\nu_{max}^{Nujol}$ (cm$^{-1}$): 3350, 1640, 1545, 1070.
NMR (D$_2$O): δ: 0.6–2.0 (m, 11H, cyclohexyl ring protones).

(2) 3.8 g of 1-(2-chloroethyl)-3-cyclohexylmethyl-3-(D-galactopyranosyl)urea and 5 g of nitrogen tetroxide gas are treated in the same manner as described in Example 23-(2). 2.8 g of 1-(2-chloroethyl)-1-nitroso-3-cyclohexylmethyl-3-(D-galactopyranosyl)urea are thereby obtained as pale yellow poder.

M.p. 68° C. (decomp.).
IR$\nu_{max}^{Nujol}$ (cm$^{-1}$): 3400, 1690, 1080.
NMR (d$_6$-DMSO) δ: 0.6–2.0 (m, 11H, cyclohexyl ring protones).
$[\alpha]_D^{22}$ −11.5° (C=1.0, methanol).

EXAMPLE 26

(1) 3.6 g of D-galactose, 3.2 g of benzylamine and 3.0 g of 2-chloroethyl isocyanate are treated in the same manner as described in Example 23-(1). 4.9 g of 1-(2-chloroethyl)-3-benzyl-3-(D-galactopyranosyl)urea are thereby obtained as colorless caramel.

IR$\nu_{max}^{Nujol}$ (cm$^{-1}$): 3350, 1640, 1540, 1080.
NMR (D$_2$O) δ: 4.73

(s, 2H, —CH₂— 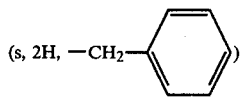)

7.30 (s, 5H, phenyl protons).

(2) 3.8 g of 1-(2-chloroethyl)-3-benzyl-3-(D-galactopyranosyl)urea and 5 g of nitrogen tetroxide gas are treated in the same manner as described in Example 23-(2). 2.8 g of 1-(2-chloroethyl)-1-nitroso-3-benzyl-3-(D-galactopyranosyl)urea are thereby obtained as yellow caramel.

IR$\nu_{max}^{CHCl_3}$ (cm$^{-1}$): 3380, 1695, 1080.
NMR (d₆-DMSO) δ: 4.64

(s, 2H, —CH₂— 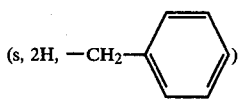)

7.29 (s, 5H, phenyl protons).
$[\alpha]_D^{15}$ −22.6° (C=1.5, methanol).

EXAMPLE 27

(1) 3.6 g of D-galactose, 4.0 g of tetrahyddrofurfurylamine and 2.5 g of 2-chloroethyl isocyanate are treated in the same manner as described in Example 23-(1). 5.0 g of 1-(2-chloroethyl)-3-tetrahydrofurfuryl-3-(D-galactopyranosyl)urea are thereby obtained as colorless caramel.

IR$\nu_{max}^{Nujol}$ (cm$^{-1}$): 3370, 1635, 1540, 1070, 1040.
NMR (D₂O) δ: 1.8–2.3

(m, 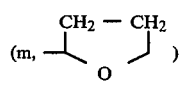)

(2) 3.7 g of 1-(2-chloroethyl)-3-tetrahydrofurfuryl-3-(D-galactopyranosyl)urea and 6 g of nitrogen tetroxide gas are treated in the same manner as described in Example 23-(2). 2.9 g of 1-(2-chloroethyl)-1-nitroso-3-tetrahydrofurfuryl-3-(D-galactopyranosyl)urea are thereby obtained as yellow caramel.

IR$\nu_{max}^{CHCl_3}$ (cm$^{-1}$): 3380, 1700, 1060.
NMR (D₂O) δ: 1.75–2.25

(m, 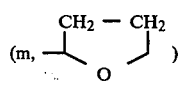)

$[\alpha]_D^{16}$ +16.6° (C=1.3, methanol).

EXAMPLE 28

(1) 3.6 g of D-galactose, 5.7 g of (3-morpholinopropyl)amine and 3.0 g of 2-chloroethyl isocyanate are treated in the same manner as described in Example 23-(1). 3.5 g of 1-(2-chloroethyl)-3-(3-morpholinopropyl)-3-(D-galactopyranosyl)urea are thereby obtained as colorless caramel.

IR $\nu_{max}^{Nujol}$ (cm$^{-1}$): 3350, 1640, 1545, 1070
NMR (D₂O) δ: 1.8–2.3

(m, 2H, 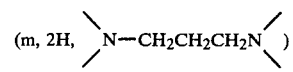)

2.7–3.2

(m, 6H, —CH₂—N 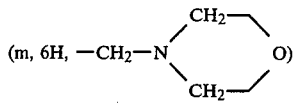)

(2) 4.1 g of 1-(2-chloroethyl)-3-(3-morpholinopropyl)-3-(D-galactopyranosyl)urea and 5 g of nitrogen tetroxide gas are treated in the same manner as described in Example 23-(2). 2.4 g of 1-(2-chloroethyl)-1-nitroso-3-(3-morpholinopropyl)-3-(D-galactopyranosyl)urea are thereby obtained as yellow caramel.

IR $\nu_{max}^{film}$ (cm$^{-1}$): 3400, 1700, 1120, 1070.
NMR (D₂O) δ: 1.8–2.3

(m, 2H, 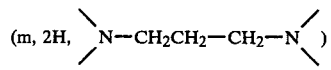)

2.6–3.0

(m, 6H, —CH₂—N 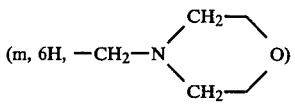)

$[\alpha]_D^{20}$ +12.6° (C=1.4, methanol).

EXAMPLE 29

(1) 5.5 g of D-galactose, 3.8 g of furfurylamine and 3.5 g of 2-chloroethyl isocyanate are treated in the same manner as described in Example 23-(1). 6.7 g of 1-(2-chloroethyl)-3-furfuryl-3-(D-galactopyranosyl)urea are thereby obtained as colorless powder.

IR $\nu_{max}^{Nujol}$ (cm$^{-1}$): 3350, 1640, 1530, 1060
NMR (D₂O) δ: 4.60

(s, 2H, —CH₂— 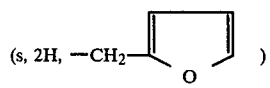)

6.45 (m, 2H, furan ring protons), 7.45 (m, 1H, furan ring proton).

(2) 3.6 g of 1-(2-chloroethyl)-3-furfuryl-3-(D-galactopyranosyl)urea and 5 g of nitrogen tetroxide gas are treated in the same manner as described in Example 23-(2). 2.8 g of 1-(2-chloroethyl)-1-nitroso-3-furfuryl-3-(D-galactopyranosyl)urea are thereby obtained as yellow caramel.

IR $\nu_{max}^{liq.}$ (cm$^{-1}$): 3380, 1690, 1070
NMR (D₂O) δ: 5.15 (d, 1H, C₁-H), 6.40 (m, 2H, furan ring protons), 7.40 (m, 1H, furan ring proton).
$[\alpha]_D^{20}$ −2.5° (C=1.2, methanol)

EXAMPLE 30

(1) 3.0 g of L-arabinose, 2.2 g of cyclopropylmethylamine and 2.5 g of 2-chloroethyl isocyanate are treated in the same manner as described in Example 23-(1). 2.4 g of 1-(2-chloroethyl)-3-cyclopropylmethyl-3-(L-arabinopyranosyl) urea are thereby obtained as colorless caramel.

IR $\nu_{max}^{Nujol}$ (cm$^{-1}$): 3350, 1640, 1535, 1060
NMR (D$_2$O) δ: 0.35–0.75

(m, 4H, 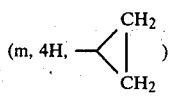

1.05–1.45

(m, 1H, —CH 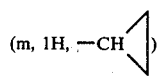

(2) 3.1 g of 1-(2-chloroethyl)-3-cyclopropylmethyl-3-(L-arabinopyranosyl)urea and 5 g of nitrogen tetroxide gas are treated in the same manner as described in Example 23-(2). 2.4 g of 1-(2-chloroethyl)-1-nitroso3-cyclopropylmethyl-3-(L-arabinopyranosyl)urea are thereby obtained as yellow caramel.

IR $\nu_{max}^{CHCl_3}$ (cm$^{-1}$): 3420, 1700, 1090
NMR (D$_2$O) δ: 0.2–0.8

(m, 4H, 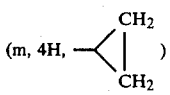

0.9–1.4

(m, 1H, —CH 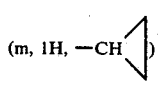

$[\alpha]_D^{20} + 54.7°$ (C=1.2, methanol)

EXAMPLE 31

(1) A mixture of 3.0 g of L-arabinose, 4.3 g of benzylamine and 10 ml of methanol is heated at 60° C. for one hour under stirring. After the reaction, the mixture is condensed to dryness under reduced pressure and the residue is washed with ether, whereby 4.7 g of 1-benzylamino-1-deoxy-L-arabinose are obtained as a crude product. 4.7 g of said crude product are dissolved in 30 ml of methanol, and a solution of 2.5 g of 2-chloroethyl isocyanate in 10 ml of tetrahydrofuran is added dropwise thereto at 0° to 5° C. The solution is stirred at room temperature for one hour. Then, the reaction solution is condensed under reduced pressure, and the residue thus obtained is dissolved in 15 ml of formic acid. The formic acid solution is allowed to stand at room temperature for 15 minutes, and 150 ml of ether-n-hexane (3:1) are added thereto. The resultant oil is collected by decantation, washed with ether and then purified by silica gel chromatography (Solvent: chloroform-ethyl acetate-methanol (2:5:1)). 6.2 g of 1-(2-chloroethyl)-3-benzyl-3-(L-arabinopyranosyl)urea are thereby obtained as colorless caramel.

IR $\nu_{max}^{Nujol}$ (cm$^{-1}$): 3350, 1640, 1530, 1090.
NMR (d$_6$-DMSO) Γ: 7.30, (s, phenyl protons).

(2) 3.4 g of 1-(2-chloroethyl)-3-benzyl-3-(L-arabinopyranosyl)urea are dissolved in a mixture of 60 ml of tetrahydrofuran and 60 ml of methylene chloride, and 15 g of sodium carbonate anhydrate are added thereto. 5 g of nitrogen tetroxide gas are introduced into the mixture for 10 minutes under ice-cooling and stirring. The mixture is further stirred at the same temperature for 10 minutes. After the reaction, 10 ml of methanol and 3 ml of water are added to the mixture, and the aqueous mixture is stirred vigorously for 10 minutes. Said aqueous mixture is dried and filtered. The filtrate is evaporated to remove solvent. Then, the residue obtained is purified by silica gel chromatography (Solvent: ethyl acetate-chloroform-methanol (5:2:1)). 2.8 g of 1-(2-chloroethyl)-1-nitroso-3-benzyl-3-(L-arabinopyranosyl)urea are thereby obtained as yellow caramel.

IR $\nu_{max}^{Nujol}$ (cm$^{-1}$): 3400, 1695, 1070.
NMR (d$_6$-DMSO)δ: 4.70

(s, 2H, —CH$_2$— 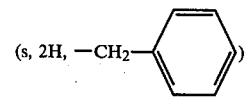

4.86 (d, 1H, C$_1$-H) 7.30 (s, 5H, phenyl protons).
$[\alpha]_D^{22}$ −15.6° (C=2.0, methanol).

EXAMPLE 32

(1) 3.0 g of L-arabinose, 3.0 g of p-methoxybenzylamine and 2.5 g of 2-chloroethyl isocyanate are treated in the same manner as described in Example 31-(1). 5.6 g of 1-(2-chloroethyl)-3-(p-methoxybenzyl)-3-(L-arabinopyranosyl)urea are thereby obtained as colorless caramel.

IR $\nu_{max}^{Nujol}$ (cm$^{-1}$): 3350, 1630, 1520, 1080.
NMR (d$_6$-DMSO)δ: 3.70 (s, 3H, OC$\underline{H}_3$). 7.03 (AB$_q$, 4H, phenyl protons).

(2) 3.7 g of 1-(2-chloroethyl)-3-(p-methoxybenzyl)-3-(L-arabinopyranosyl)urea and 5.0 g of nitrogen tetroxide gas are treated in the same manner as described in Example 31-(2). 2.5 g of 1-(2-chloroethyl)-1-nitroso-3-(p-methoxybenzyl)-3-(L-arabinopyranosyl)urea are thereby obtained as yellow caramel.

IR $\nu_{max}^{Nujol}$ (cm$^{-1}$): 3400, 1695, 1510, 1080.
NMR (D$_2$O)δ: 3.70, (s, 3H, OCH$_3$), 4.60

(s, 2H, —CH$_2$— 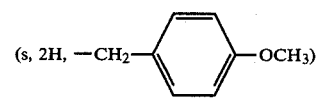 —OCH$_3$)

4.80 (d, 1H, C$_1$-H), 7.03 (AB$_q$, 4H, phenyl protons).
$[\alpha]_D^{22}$ −16.6° (C=1.6, methanol).

EXAMPLE 33

(1) 4.5 g of L-arabinose, 2.5 g of 2-propenylamine and 3.5 g of 2-chloroethyl isocyanate are treated in the same manner as described in Example 31-(1). 5.5 g of 1-(2-chloroethyl)-3-(2-propenyl)-3-(L-arabinopyranosyl)urea are thereby obtained as colorless powder.

IR$\nu_{max}^{Nujol}$ (cm$^{-1}$): 3340, 1630, 1530, 1080.
NMR (D$_2$O)δ: 5.0–6.3 (m, 4H, —C$\underline{H}$=C$\underline{H}_2$, C$_1$—H).

(2) 3.2 g of 1-(2-chloroethyl)-3-(2-propenyl)-3-(L-arabinopyranosyl)urea and 5 g of nitrogen tetroxide gas are treated in the same manner as described in Example 31-(2). 2.3 g of 1-(2-chloroethyl)-1-nitroso-3-(2-propenyl)-3-(L-arabinopyranosyl)urea are thereby obtained as yellow caramel.

IR $\nu_{max}^{Nujol}$ (cm$^{-1}$): 3400, 1700, 1080,

NMR (D₂O)δ: 4.9–6.3 (m, 4H, —C$\underline{H}$=C$\underline{H}_2$, C₁—H),
[α]$_D^{20}$+12.8° (C=1.3, methanol).

(3) A mixture of 5.3 g of 1-(2-chloroethyl)-1-nitroso-3-(2-propenyl)-3-(L-arabinopyranosyl)urea, 5.9 g of meta-chloroperbenzoic acid, 50 ml of methylene chloride and 50 ml of benzene is stirred at room temperature for 3 hours. After the reaction, the mixture is condensed under reduced pressure. The residue obtained is washed with ether and then purified by silica gel chromatography (Solvent: ethyl acetate). 0.9 g of 1-(2-chloroethyl)-1-nitroso-3-(oxiran-2-yl-methyl)-3-(L-arabinopyranosyl)urea is thereby obtained as yellow caramel.

IR$\nu_{max}^{CHCl_3}$ (cm⁻¹): 3420, 1700, 1080.
NMR (D₂O)δ: 2.70–3.05

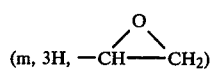

4.20 (t, 2H, —N(NO)C$\underline{H}_2$—)
[α]$_D^{28}$+38.4° (C=0.5, methanol)

EXAMPLE 34

(1) 3.0 g of L-arabinose, 2.7 g of (thiophen-2-yl-methyl)amine and 2.5 of 2-chloroethyl isocyanate are treated in the same manner as described in Example 31-(1). 4.1 g of 1-(2-chloroethyl)-3-(thiopen-2-yl-methyl)-3-(L-arabinopyranosyl)urea are thereby obtained as colorless powder.

M.p. 135°–140° C.
IR$\nu_{max}^{Nujol}$ (cm⁻¹): 3490, 3395, 3280, 1605, 1550, 1095 1065.
NMR (D₂O)δ: 7.0–7.3

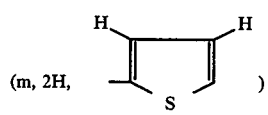

7.4–7.6

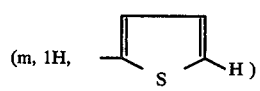

(2) 3.5 g of 1-(2-chloroethyl)-3-(thiophen-2-yl-methyl)-3-(L-arabinopyranosyl)urea and 5.0 g of nitrogen tetroxide gas are treated in the same manner as described in Example 31-(2). 3.1 g of 1-(2-chloroethyl)-1-nitroso-3-(thiophen-2-yl-methyl)-3-(L-arabinopyranosyl)urea are thereby obtained as yellow powder.

M.p. 63°–70° C. (decomp.)
IR$\nu_{max}^{CHCl_3}$ (cm⁻¹): 3400, 1700, 1080.
NMR (D₂O)δ: 7.0–7.3

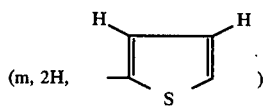

7.4–7.6

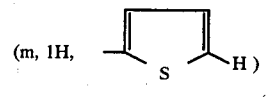

[α]$_D^{26}$+14.1° (C=1.0, methanol)

EXAMPLE 35

(1) 3.0 g of D-ribose, 2.2 g of cyclopropylmethylamine and 2.5 g of 2-chloroethyl isocyanate are treated in the same manner as described in Example 31-(1). 4.2 g of 1-(2-chloroethyl)-3-cyclopropylmethyl-3-(D-ribofuranosyl)urea are thereby obtained as colorless caramel.

IR$\nu_{max}^{neat}$ (cm⁻¹): 3350, 1630, 1530, 1080.
NMR (D₂O)δ: 0.20–0.70

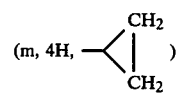

0.90–1.35

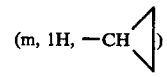

(2) 3.1 g of 1-(2-chloroethyl)-3-cyclopropylmethyl-3-(D-ribofuranosyl)urea and 5 g of nitrogen tetroxide gas are treated in the same manner as described in Example 31-(2). 2.3 g of 1-(2-chloroethyl)-1-nitroso-3-cyclopropylmethyl-3-(D-ribofuranosyl)urea are thereby obtained as yellow liquid.

IR$\nu_{max}^{Nujol}$ (cm⁻¹): 3450, 1700, 1080.
NMR (D₂O)δ: 0.20–0.70

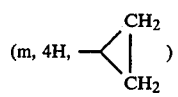

1.00–1.40

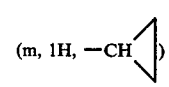

[α]$_D^{25}$−8.2° (C=1.2, methanol).

EXAMPLE 36

(1) 3.0 g of D-ribose, 2.8 g of furfurylamine and 2.5 g of 2-chloroethyl isocyanate are treated in the same manner as described in Example 31-(1). 4.3 g of 1-(2-chloroethyl)-3-furfuryl-3-(D-ribofuranosyl)urea are thereby obtained as colorless caramel.

IR$\nu_{max}^{CHCl_3}$ (cm⁻¹): 3400, 1650, 1520, 1080.
NMR (D₂O)δ: 6.40

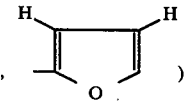

7.45 (m, 1H, 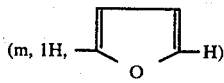)

(2) 3.3 g of 1-(2-chloroethyl)-3-furfuryl-3-(D-ribofuranosyl)urea and 5.0 of nitrogen tetroxide gas are treated in the same manner as described in Example 31-(2). 2.2 g of 1-(2-chloroethyl)-1-nitroso-3-furfuryl-3-(D-ribofuranosyl)urea are thereby obtained as yellow powder.

M.p. 67° C. (decomp.)
IR$\nu_{max}^{Nujol}$ (cm$^{-1}$): 3450, 1700, 1070, 1040, 1010,
NMR (D$_2$O)δ: 6.39

(m, 2H, 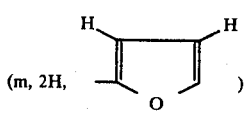)

7.44

(m, 1H, 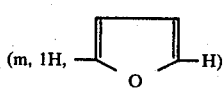)

$[\alpha]_D^{22} -2.8°$ (C=0.9, methanol)

EXAMPLE 37

(1) 3.0 g of D-xylose, 2.2 g of cyclopropylmethylamine and 2.5 g of 2-chloroethyl isocyanate are treated in the same manner as described in Example 31-(1). 3.8 g of 1-(2-chloroethyl)-1-cyclopropylmethyl-3-(D-xylopyranosyl)urea are thereby obtained as colorless caramel.

IR$\nu_{max}^{Nujol}$ (cm$^{-1}$): 3350, 1640, 1530, 1050.
NMR (D$_2$O)δ: 0.20–0.68

(m, 4H, 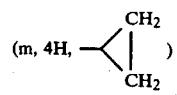)

0.86–1.30

(m, 1H, —CH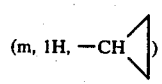)

4.98 (d, 1H, C$_1$H)

(2) 3.1 g of 1-(2-chloroethyl)-3-cyclopropylmethyl-3-(D-xylopyranosyl)urea and 5 g of nitrogen tetroxide gas are treated in the same manner as described in Example 31-(2). 2.2 g of 1-(2-chloroethyl)-1-nitroso-3-cyclopropylmethyl-3-(D-xylopyranosyl)urea are thereby obtained as yellow caramel.

IR$\nu_{max}^{CHCl_3}$ (cm$^{-1}$): 3400, 1700, 1080
NMR (D$_2$O) δ: 0.20–0.70

(m, 4H, 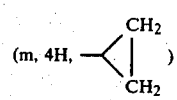)

0.94–1.40

(m, 1H, —CH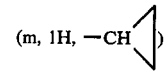)

4.18 (t, 2H, —N(NO)CH$_2$Cl)
$[\alpha]_D^{25} +11.0°$ (C=1.5, methanol)

EXAMPLE 38

(1) 3.6 g of D-glucose, 4.0 g of tetrahydrofufrurylamine and 2.5 g of 2-chloroethyl isocyanate are treated in the same manner as described in Example 31-(1). 5.2 g of 1-(2-chloroethyl)-3-tetrahydrofurfuryl-3-(D-glucopyranosyl)urea are thereby obtained as colorless caramel.

IR$\nu_{max}^{Nujol}$ (cm$^{-1}$): 3350, 1640, 1540, 1070.
NMR (D$_2$O)δ: 1.50–2.16

(m, 4H, 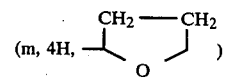)

5.04 (d, 1H, C$_1$-H)
(2) 3.7 g of 1-(2-chloroethyl)-3-tetrahydrofurfuryl-3-(D-glucopyranosyl)urea and 6 g of nitrogen tetroxide gas are treated in the same manner as described in Example 31-(2). 1.1 g of 1-(2-chloroethyl)-1-nitroso-3-tetrahydrofurfuryl-3-(D-glucopyranosyl)urea are thereby obtained as yellow caramel.

IR$\nu_{max}^{CHCl_3}$ (cm$^{-1}$): 3400, 1695, 1070.
NMR (D$_2$O)δ: 1.56–2.10

(m, 4H, 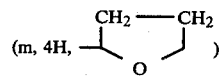)

4.20 (t, 2H, —N(NO)CH$_2$—), 4.96 (d, 1H, C$_1$—H).
$[\alpha]_D^{28} +21.6°$ (C=1.0, methanol)

EXAMPLE 39

(1) 3.6 g of D-mannose, 2.2 g of cyclopropylmethylamine and 2.5 g of 2-chloroethyl isocyanate are treated in the same manner as described in Example 31-(1). 4.3 g of 1-(2-chloroethyl)-3-cyclopropylmethyl-3-(D-mannopyranosyl)urea are thereby obtained as colorless caramel.

IR$\nu_{max}^{Nujol}$ (cm$^{-1}$): 3350, 1630, 1530, 1060.
NMR (D$_2$O)δ: 0.20–0.72

(m, 4H, 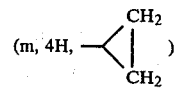)

0.90–1.26

(m, 1H, —CH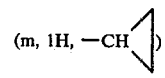)

(2) 3.4 g of 1-(2-chloroethyl)-3-cyclopropylmethyl-3-(D-mannopyranosyl)urea and 5 g of nitrogen tetroxide gas are treated in the same manner as described in Example 31-(2). 2.3 g of 1-(2-chloroethyl)-1-nitroso-3-cyclopropylmethyl-3-(D-mannopyranosyl)urea are thereby obtained as yellow caramel.

IR$\nu_{max}^{CHCl_3}$ (cm$^{-1}$): 3400, 1690, 1080.
NMR (D$_2$O)δ: 0.20–0.68

(m, 4H, 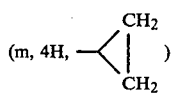)

1.04–1.36

(m, 1H, 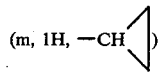)

$[\alpha]_D^{27} + 26.3°$ (C=1.3, methanol).

EXAMPLE 40

3.7 g of 1-(2-chloroethyl)-3-tetrahydrofurfuryl-3-(D-galactopyranosyl)urea are dissolved in 15 ml of formic acid, and 2.1 g of sodium nitrite are added gradually thereto at 0° C. for one hour under stirring. The mixture is further stirred at the same temperature for 30 minutes. 100 ml of etherhexane (1:1) are added to the reaction mixture. The resultant oil is washed with ether. Then, 100 ml of ethyl acetate-methanol (10:1) are added to said oil, and insoluble materials are removed by filtration. The filtrate is evaporated to remove solvent, and the residue obtained is purified by silica gel chromatography (Solvent: ethyl acetate-chloroform-methanol (5:2:1)). 0.9 g of 1-(2-chloroethyl)-1-nitroso-3-tetrahydrofurfuryl-3-(D-galactopyranosyl)urea are thereby obtained as yellow caramel.

$[\alpha]_D^{16} + 16.6°$ (C=1.2, methanol)

EXAMPLE 41

3.1 g of 1-(2-chloroethyl)-3-cyclopropylmethyl-3-(L-arabinopyranosyl)urea are dissolved in 15 ml of formic acid, and 1.5 g of sodium nitrite are added gradually thereto at 0° C. for one hour under stirring. The mixture is further stirred at the same temperature for one hour. After the reaction, 15 ml of ethanol are added to the reaction mixture. Said mixture is neutralized with potassium carbonate under ice-cooling. Then, 150 ml of ethyl acetate are added to the mixture, and insoluble materials are removed by filtration. The filtrate is washed with an aqueous sodium bicarbonate solution, dried and evaporated to remove solvent. The residue thus obtained is purified by silica gel chromatography (Solvent: ethyl acetate-chloroform-methanol (5:2:1)). 1.5 g of 1-(2-chloroethyl)-1-nitroso-3-cyclopropylmethyl-3-(L-arabinopyranosyl)urea are thereby obtained as yellow caramel.

$[\alpha]_D^{20} + 54.7°$ (C=1.2, methanol)

EXAMPLE 42

3.1 g of 1-(2-chloroethyl)-3-cyclopropylmethyl-3-(D-ribofuranosyl)urea and 1.5 g of sodium nitrite are treated in the same manner as described in Example 41. 1.6 g of 1-(2-chloroethyl)-1-nitroso-3-cyclopropylmethyl-3-(D-ribofuranosyl)-urea are thereby obtained as yellow liquid.

$[\alpha]_D^{25} - 8.2°$ (C=1.2, methanol)

What we claim is:

1. A nitrosourea compound of the formula:

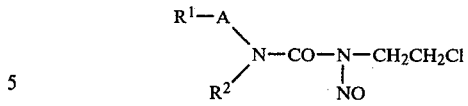

wherein R$^1$ is an alicyclic group having 3 to 6 carbon atoms, phenyl, phenyl substituted with one to 3 substituents selected from the class consisting of halogen, lower alkyl, lower alkoxy, hydroxy and nitro, a heteromonocyclic group selected from the class consisting of oxiranyl, tetrahydrofuryl, 1,3-dioxolanyl, 1,4-dioxanyl, morpholino, tetrahydro-S,S-dioxo-thienyl, furyl, thienyl and pyridyl; R$^2$ is aldo-pentofuranosyl, aldo-pentopyranosyl, aldo-hexopyranosyl or O-aldo-hexopyranosyl-(1→4)-aldo-hexopyranosyl; and A is a single bond, straight or branched alkylene having one to 3 carbon atoms.

2. The compound of claim 1, in which R$^2$ is D-aldopentofuranosyl, D- or L-aldo-pentopyranosyl, D- or L-aldo-hexopyranosyl or O-D-aldo-hexopyranosyl-(1→4)-D-aldo-hexopyranosyl.

3. The compound of claim 2, in which R$^1$ is an alicyclic group selected from the class consisting of cyclopropyl, cyclopentyl and cyclohexyl, phenyl, a substituted phenyl selected from the class consisting of monochlorophenyl, monomethylphenyl, trimethylphenyl, monomethoxyphenyl, dimethoxyphenyl, trimethoxyphenyl, monohydroxyphenyl and mononitrophenyl, or a heteromonocyclic group selected from the class consisting of oxiranyl, tetrahydrofuryl, 1,3-dioxolanyl, 1,4-dioxanyl, morpholino, tetrahydro-S,S-dioxothienyl, furyl, thienyl and pyridyl; and R$^2$ is D-aldo-pentofuranosyl, D- or L-aldo-pentopyranosyl, D-aldo-hexopyranosyl or O-D-aldo-hexopyranosyl-(1→4)-D-aldo-hexopyranosyl.

4. The compound of claim 3, in which R$^1$ is an alicyclic group selected from the class consisting of cyclopropyl, cyclopentyl and cyclohexyl, phenyl, a substituted phenyl selected from the class consisting of monochlorophenyl, monomethylphenyl, trimethylphenyl and monomethoxyphenyl, or a heteromonocyclic group selected from the class consisting of oxiranyl, tetrahydrofuryl, furyl and thienyl; and A is a single bond or alkylene having one or two carbon atoms.

5. The compound of claim 4, in which R$^1$ is an alicyclic group selected from the class consisting of cyclopropyl, cyclopentyl and cyclohexyl, phenyl, a substituted phenyl selected from the class consisting of p-chlorophenyl, p-methylphenyl, 2,4,6-trimethylphenyl and p-methoxyphenyl, or a heteromonocyclic group selected from the class consisting of oxiran-2-yl, tetrahydrofuran-2-yl, furan-2-yl and thiophen-2-yl.

6. The compound of claim 4, in which R$^2$ is D-ribofuranosyl, L-arabinopyranosyl, D-xylopyranosyl, D-glucopyranosyl, D-galactopyranosyl, D-mannopyranosyl or O-α-D-glucopyranosyl-(1→4)-D-glucopyranosyl.

7. The compound of claim 4, in which R$^2$ is D-ribofuranosyl, L-arabinopyranosyl, D-xylopyranosyl, D-glucopyranosyl, D-galactopyranosyl or O-α-D-glucopyranosyl-(1→4)-D-glucopyranosyl.

8. The compound of claim 5, in which R$^2$ is D-ribofuranosyl, L-arabinopyranosyl, D-xylopyranosyl, D-glucopyranosyl, D-galactopyranosyl or O-α-D-glucopyranosyl-(1→4)-D-glucopyranosyl.

9. The compound of claim 4, in which $R^2$ is L-arabinopyranosyl, D-galactopyranosyl or O-α-D-glucopyranosyl-(1→4)-D-glucopyranosyl.

10. The compound of claim 5, in which $R^2$ is L-arabinopyranosyl, D-galactopyranosyl or O-α-D-glucopyranosyl-(1→4)-D-glucopyranosyl.

11. The compound of claim 6, 7, 8, 9 or 10, in which $R^1$ is an alicyclic group selected from the class consisting of cyclopropyl, cyclopentyl or cyclohexyl, and A is a single bond or alkylene having one or two carbon atoms.

12. The compound of claim 6, 7, 8, 9 or 10, in which $R^1$ is phenyl or a substituted phenyl selected from the class consisting of p-chlorophenyl, p-methylphenyl, 2,4,6-trimethylphenyl and p-methoxyphenyl, and A is alkylene having one or two carbon atoms.

13. The compound of claim 6, 7, 8, 9 or 10, in which $R^1$ is a heteromococyclic group selected from the class consisting of oxiran-2-yl, tetrahydrofuran-2-yl, furan-2-yl and thiophen-2-yl, and A is methylene.

14. The compound of claim 6, 7, 8, 9 or 10, in which $R^1$ is cyclopropyl, cyclohexyl, phenyl, p-methylphenyl, 2,4,6-trimethylphenyl, p-methoxyphenyl, oxiran-2-yl, tetrahydrofuran-2yl, furan-2-yl or thiophen-2-yl, and A is a single bond, methylene, ethylene or methylmethylene.

15. The compound of claim 14, in which $R^1$ is cyclopropyl, $R^2$ is L-arabinopyranosyl or O-α-D-glucopyranosyl-(1→4)-D-glucopyranosyl, and A is methylene.

16. The compound of claim 14, in which $R^1$ is cyclopropyl or cyclohexyl, $R^2$ is D-galactopyranosyl, and A is single bond or methylene.

17. The compound of claim 14, in which $R^1$ is phenyl, $R^2$ is O-α-D-glucopyranosyl-(1→4)-D-glucopyranosyl, and A is methylene, ethylene or methylmethylene.

18. A compound of claim 14, in which $R^1$ is phenyl, $R^2$ is D-galactopyranosyl or L-arabinopyranosyl, and A is methylene.

19. The compound of claim 14, in which $R^1$ is p-methylphenyl, 2,4,6-trimethylphenyl or p-methoxyphenyl, $R^2$ is L-arabinopyranosyl or O-α-D-glucopyranosyl-(1→4)-D-glucopyranosyl, and A is methylene.

20. The compound of claim 14, in which $R^1$ is tetrahydrofuran-2-yl, furan-2-yl or thiophen-2-yl, $R^2$ is O-α-D-glucopyranosyl-(1→4)-D-glucopyranosyl, and A is methylene.

21. The compound of claim 14, in which $R^1$ is oxiran-2-yl, tetrahydrofuran-2-yl or thiophen-2-yl, $R^2$ is D-galactopyranosyl or L-arabinopyranosyl, and A is methylene.

22. The compound of claim 15 which is 1-(2-chloroethyl)-1-nitroso-3-cyclopropylmethyl-3-(L-arabinopyranosyl)urea.

23. The compound of claim 16 which is 1-(2-chloroethyl)-1-nitroso-3-cyclopropylmethyl-3-(D-galactopyranosyl)urea.

24. The compound of claim 16 which is 1-(2-chloroethyl)-1-nitroso-3-cyclohexyl-3-(D-galactopyranosyl)urea.

25. The compound of claim 17 which is 1-(2-chloroethyl)-1-nitroso-3-benzyl-3-[O-α-D-glucopyranosyl-(1→4)-D-glucopyranosyl]urea.

26. The compound of claim 17 which is 1-(2-chloroethyl)-1-nitroso-3-phenethyl-3-[O-α-D-glucopyranosyl-(1→4)-D-glucopyranosyl]urea.

27. The compound of claim 17 which is 1-(2-chloroethyl)-1-nitroso-3-(α-methylbenzyl)-3-[O-α-D-glucopyranosyl-(1→4)-D-glucopyranosyl]urea.

28. The compound of claim 18 which is 1-(2-chloroethyl)-1-nitroso-3-benzyl-3-(L-arabinopyranosyl)urea.

29. The compound of claim 19 which is 1-(2-chloroethyl)-1-nitroso-3-(p-methoxybenzyl)-3-)L-arabinopyranosyl)urea.

30. The compound of claim 19 which is 1-(2-chloroethyl)-1-nitroso-3-(p-methylbenzyl)-3-[O-α-D-glucopyranosyl-(1→4)-D-glucopyranosyl]urea.

31. The compound of claim 19 which is 1-(2-chloroethyl)-1-nitroso-3-(2,4,6-trimethylbenzyl)-3-[O-α-D-glucopyranosyl-(1→4)-D-glucopyranosyl]urea.

32. The compound of claim 19 which is 1-(2-chloroethyl)-1-nitroso-3-(p-methoxybenzyl)-3-[O-α-D-glucopyranosyl-(1→4)-D-glucopyranosyl]urea.

33. The compound of claim 20 which is 1-(2-chloroethyl)-1-nitroso-3-tetrahydrofurfuryl-3-[O-α-D-glucopyranosyl-(1→4)-D-glucopyranosyl]urea.

34. The compound of claim 20 which is 1-(2-chloroethyl)-1-nitroso-3-furfuryl-3-[O-α-D-glucopyranosyl-(1→4)-D-glucopyranosyl]urea.

35. The compound of claim 20 which is 1-(2-chloroethyl)-1-nitroso-3-(thiophen-2-yl-methyl)-3-[O-α-D-glucopyranosyl-(1→4)-D-glucopyranosyl]urea.

36. The compound of claim 21 which is 1-(2-chloroethyl)-1-nitroso-3-tetrahydrofurfuryl-3-(D-galactopyranosyl)urea.

37. The compound of claim 21 which is 1-(2-chloroethyl)-1-nitroso-3-(oxiran-2-yl-methyl)-3-(L-arabinopyranosyl)-urea.

38. The compound of claim 21 which is 1-(2-chloroethyl)-1-nitroso-3-(thiophen-2-yl-methyl)-3-(L-arabinopyranosyl)urea.

39. The compound of the formula:

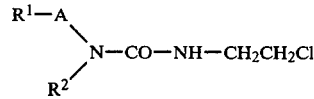

wherein $R^1$ is an alicyclic group having 3 to 6 carbon atoms, phenyl, phenyl substituted with one to 3 substituents selected from the class consisting of halogen, lower alkyl, lower alkoxy, hydroxy and nitro, or a heteromonocyclic group selected from the class consisting of oxiranyl, tetrahydrofuryl, 1,3-dioxolanyl, 1,4-dioxanyl, morpholino, tetrahydro-S,S-dioxo-thienyl, furyl, thienyl and pyridyl; $R^2$ is aldo-pentofuranosyl, aldo-pentopyranosyl, aldo-hexopyranosyl or O-aldo-hexopyranosyl-(1→4)-aldo-hexopyranosyl; and A is a single bond or straight or branched alkylene having one to 3 carbon atoms.

40. The compound of claim 39, in which $R^1$ is an alicyclic group selected from the class consisting of cyclopropyl, cyclopentyl and cyclohexyl, phenyl, a substituted phenyl selected from the class consisting of monochlorophenyl, monomethylphenyl, trimethylphenyl and monomethoxyphenyl, or a heteromonocyclic group selected from the class consisting of oxiranyl, tetrahydrofuryl, furyl and thienyl; $R^2$ is D-aldo-pentofuranosyl, D- or L-pentopyranosyl, D-aldo-hexopyranosyl or O-aldo-hexopyranosyl-(1→4)-D-aldo-hexopyranosyl; and A is a single bond or alkylene having one or two carbon atoms.

41. A therepeutic composition which comprises a theropeutically effective amount of a nitrosourea compound of the formula:

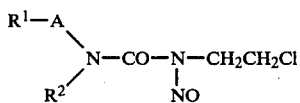

wherein $R^1$ is an alicyclic group having 3 to 6 carbon atoms, phenyl, phenyl substituted with one to 3 substituents selected from the class consisting of halogen, lower alkyl, lower alkoxy, hydroxy and nitro, or a heteromonocyclic group selected from the class consisting of oxiranyl, tetrahydrofuryl, 1,3-dioxolanyl, 1,4-dioxanyl, morpholino, tetrahydro-S.S-dioxo-thienyl, furyl, thienyl and pyridyl; $R^2$ is aldo-pentofuranosyl, aldo-pentopyranosyl, aldo-hexopyranosyl or O-aldo-hexopyranosyl-(1→4)-aldo-hexopyranosyl; and A is a single bond or straight or branched alkylene having one to 3 carbon atoms, and a pharmaceutically acceptable carrier therefor.

42. The therapeutic composition of claim 41, in which $R^1$ is an alicyclic group selected from the class consisting of cyclopropyl, cyclopentyl and cyclohexyl, phenyl, a substituted phenyl selected from the class consisting of monochlorophenyl, monomethylphenyl, trimethylphenyl and monomethoxyphenyl; or a heteromonocyclic group selected from the class consisting of oxiranyl, tetrahydrofuryl, furyl and thienyl, $R^2$ is D-aldo-pentofuranosyl, D- or L-aldopentopyranosyl, D-aldo-hexopyranosyl or O-D-aldo-hexopyranosyl-(1→4)-D-aldo-hexopyranosyl, and A is a single bond or alkylene having one or two carbon atoms.

43. A method of treating malignant tumor cells in test animals comprising administering to said animals a therapeutically effective amount of the compound of claim 1.

44. The method according to claim 43 wherein said amount is between about 0.1 and 30 mg/kg/day.

45. The method according to claim 44 wherein said amount is between about 0.2 and 10 mg/kg/day.

46. A method of treating leukemia in test animals comprising administering to said animals a therapeutically effective amount of the compound of claim 1.

47. The method according to claim 46 wherein said amount is between about 0.1 and 30 mg/kg/day.

48. The method according to claim 47 wherein said amount is between about 0.2 and 10 mg/kg/day.

* * * * *